US008496931B2

(12) United States Patent
Pogue et al.

(10) Patent No.: US 8,496,931 B2
(45) Date of Patent: Jul. 30, 2013

(54) MONOCLONAL ANTIBODIES AGAINST STROMAL DERIVED FACTOR-1 (SDF-1)

(75) Inventors: Sarah L. Pogue, Fremont, CA (US); Alan J. Korman, Piedmont, CA (US); Josephine M. Cardarelli, San Carlos, CA (US); Mohan Srinivasan, Cupertino, CA (US); Bingliang Chen, Alameda, CA (US); Alasdair F. Bell, Mountain View, CA (US)

(73) Assignees: Medarex, Inc., Princeton, NJ (US); Ono Pharmaceutical Co., Ltd., Osaka (JP)

( * ) Notice: Subject to any disclaimer, the term of this patent is extended or adjusted under 35 U.S.C. 154(b) by 890 days.

(21) Appl. No.: 12/377,015

(22) PCT Filed: Aug. 10, 2007

(86) PCT No.: PCT/JP2007/065991
§ 371 (c)(1),
(2), (4) Date: Apr. 24, 2009

(87) PCT Pub. No.: WO2008/018641
PCT Pub. Date: Feb. 14, 2008

(65) Prior Publication Data
US 2010/0158902 A1 Jun. 24, 2010

Related U.S. Application Data

(60) Provisional application No. 60/837,004, filed on Aug. 11, 2006.

(51) Int. Cl.
*A61K 39/395* (2006.01)
(52) U.S. Cl.
USPC .................................... 424/130.1; 530/387.1
(58) Field of Classification Search
None
See application file for complete search history.

(56) References Cited

U.S. PATENT DOCUMENTS

2005/0002939 A1* 1/2005 Zlotnik et al. ............. 424/155.1

FOREIGN PATENT DOCUMENTS

| WO | 99/50461 A1 | 10/1999 |
| WO | 03/080116 A1 | 10/2003 |
| WO | 2008/021263 A2 | 2/2008 |

OTHER PUBLICATIONS

Shirozu et al. (Genomics, vol. 28, pp. 495-500, 1995) cited on IDS filed Feb. 10, 2009.*
GenBank Accession L36033, http://www.ncbi.nlm.nih.gov/nuccore/1220365, retrieved Dec. 17, 2011.*
Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Michio Shirozu, et al.; "Structure and chromosomal localization of the human stromal cell-derived factor 1 (SDF1) gene."; Genomics.; 1995; vol. 28, No. 3; pp. 495-500.
Matthew P. Crump, et al.; "Solution structure and basis for functional activity of stromal cell-derived factor-1; dissociation of CXCR4 activation from binding and inhibition of HIV-1"; The EMBO Journal; 1997; vol. 16, No. 23; pp. 6996-7007.
Benjamin T. Suratt, et al.; "Role of the CXCR4/SDF-1 chemokine axis in circulating neutrophil homeostasis."; Blood, 2004; vol. 104, No. 2; pp. 565-571.
Extended European Search Report dated Apr. 7, 2010 in Counterpart European Application No. 07792618.6.
Salvucci et al., "Regulation of endothelial cell branching morphogenesis by endogenous chemokine stromal-derived factor-1," Blood, vol. 99, No. 8, pp. 2703-2711 (2002).
Schober et al., "Crucial Role of Stromal Cell-Derived Factor-1a in Neointima Formation After Vascular Injury in Apolipoprotein E-Deficient Mice," Circulation, vol. 108, No. 20, pp. 2491-2497 (2003).
Butler at al., "SDF-1 is both necessary and sufficient to promote proliferative retinopathy," Journal of Clinical Investigation, vol. 115, No. 1, pp. 86-93 (2005).
Cashman et al., "Stromal-derived factor 1 inhibits the cycling of very primitive human hematopoietic cells in vitro and in NOD/SCID mice," Blood, vol. 99, No. 3, pp. 792-799 (2002).
R&D Systems: "Monoclonal Anti-human/mouse CXCL12.SDF-1 Antibody," R&D Systems Catalogue at http://www.rndsystems.com/pdf/MAB310.pdf, pp. 1-2, Aug. 2007.
R&D Systems: "Anti-human CXCL12/SDF-1B Antibody," R&D Catalogue at http://www.rndsystems.com/pdf/af310na.pdf, pp. 1-2, Jul. 2005.
Sengupta et al., "Preventing Stem Cell Incorporation into Choroidal Neovascularization by Targeting Homing and Attachment Factors," Investigative Ophthalamology & Visual Science, vol. 46, No. 1, pp. 343-348 (2005).
Hernandez-Lopez et al., "CXCL12/CXCR4 signaling promotes human thymic dendritic cell survival regulating the Bcl-2/Bax ratio," Immunology Letters, vol. 120, pp. 72-78 (2008).
Plett et al., "Treatment with SDF-1 or Anti-CXCR4 Antibody Activates Human Hematopoietic Progenitor Cells and Enhances Their NOD/SCID Repopulating Potential," Blood, vol. 96, No. 11, p. 687A (2000).
Tsukada et al., "Antibody to Stromal Derived Factor-1 (SDF-1) or CS-1 Synthetic Peptide Specifically Inhibit the Protective Activity of Nurse-Like Cells on Leukemia Cell Viability In Vitro," Blood, vol. 98, No. 11, p. 234A (2001).
Office Action dated Aug. 6, 2010, issued by the European Patent Office in counterpart European Patent Application No. 07792618.6.

* cited by examiner

*Primary Examiner* — Laura B Goddard
*Assistant Examiner* — Meera Natarajan
(74) *Attorney, Agent, or Firm* — Sughrue Mion, PLLC

(57) ABSTRACT

The present disclosure provides isolated monoclonal antibodies, particularly human monoclonal antibodies, that specifically bind to SDF-1 with high affinity. Nucleic acid molecules encoding SDF-1 antibodies, expression vectors, host cells and methods for expressing the SDF-1 antibodies are also provided. Immunoconjugates, bispecific molecules and pharmaceutical compositions comprising the SDF-1 antibodies are also provided. Methods for detecting SDF-1, as well as methods for treating various B cell malignancies, including breast cancer, multiple myeloma and non-Hodgkin's lymphoma, and autoimmune disorders are disclosed.

38 Claims, 23 Drawing Sheets

Fig. 1A

Anti-SDF-1 1D3 VH
V segment: 1-24
D segment: 6-19
J segment: JH6b primer encoded

```
      E   V   Q   L   V   Q   S   G   A   E   V   K   K   P   G   A   S   V   K
  1   GAG GTG CAG CTG GTG CAG TCT GGG GCT GAG GTG AAG AAG CCT GGG GCC TCA GTG AAG

V   S   C   K   V   S   G   Y   T   L   T   T   K   L   S   V   H   W   V   R
 58   GTC TCC TGC AAG GTT TCC GGA TAC ACC CTC ACT AAA TTA TCC GTG CAC TGG GTG CGA
                                                        CDR1

Q   A   P   G   K   G   L   E   W   M   G   S   F   D   P   E   D   G   E
115   CAG GCT CCT GGA AAA GGG CTT GAG TGG ATG GGA AGT TTT GAT CCT GAA GAT GGT GAA
                                                    CDR2

T   I   Y   S   Q   R   F   Q   G   R   V   T   M   T   E   D   T   S   T
172   ACA ATC TAC TCA CAG AGG TTC CAG GGC AGA GTC ACC ATG ACC GAG GAC ACA TCT ACA
      D   T   A   Y   M   E   L   T   S   L   R   S   E   D   T   A   V   Y   Y
229   GAC ACA GCC TAC ATG GAG CTG ACC AGC CTG AGA TCT GAG GAC ACG GCC GTG TAT TAC
                                                        CDR3

C   A   T   E   G   Q   G   Q   W   L   V   A   Y   Y   G   M   D   V   W   G   Q
286   TGT GCA ACG GAG GGG CAG GGG CAG TGG CTG GTA GCC TAC TAC GGT ATG GAC GTC TGG GGC CAA
      G   T   T   V   T   V   S   S
343   GGG ACC ACG GTC ACC GTC TCC TCA
```

Fig. 1B

Anti-SDF-1 1D3 VK
V segment: L18
J segment: JK4

```
                primer encoded
        ~~~~~~~~~~~~~~~~~~~~~~
        E   I   V   L   T   Q   S   P   S   S   L   S   A   S   V   G   D   R   V
  1     GAA ATT GTG CTC ACC CAG TCT CCA TCC TCC CTG TCT GCA TCT GTA GGA GAC AGA GTC
                                            ~~~~~~~~~~~~~~~~~~~~~~~~~~~~~~~~~~~~~~~
                                            CDR1
        T   I   T   C   R   A   S   Q   G   I   S   A   L   A   W   Y   Q   Q
 58     ACC ATC ACT TGC CGG GCA AGT CAG GGC ATT AGC AGT GCT TTA GCC TGG TAT CAG CAG
        ~~~~~~~~~~~~~~~~~~~~~~~~~~~~~
                                                            ~~~~~~~~~~~~~~~~~~~~~~~
                                                            CDR2
        K   P   G   K   A   P   K   L   L   I   Y   D   A   S   S   L   E   S   G
115     AAA CCA GGG AAA GCT CCT AAG CTC CTG ATC TAT GAT GCC TCC AGT TTG GAA AGT GGG
        ~~~~~~~~~~~~~~~~~~~~~~~~~~~~~~~~~~
        V   P   S   R   F   S   G   S   G   S   G   T   D   F   T   L   T   I   S
172     GTC CCA TCA AGG TTC AGC GGC AGT GGA TCT GGG ACA GAT TTC ACT CTC ACC ATC AGC
                                                                    ~~~~~~~~~~~~~~~
                                                                    CDR3
        S   L   Q   P   E   D   F   A   T   Y   Y   C   Q   Q   F   N   S   Y   P
229     AGC CTG CAG CCT GAA GAT TTT GCA ACT TAT TAC TGT CAA CAG TTT AAT AGT TAC CCG
        ~~~~~~~~~~~~~~~
        CDR3
        L   T   F   G   G   G   T   K   V   E   I   K
286     CTC ACT TTC GGC GGA GGG ACC AAG GTG GAG ATC AAA
```

Fig. 2A

Anti-SDF-1 1H2 VH
V segment: 1-24
D segment: 6-19
J segment: JH6b

```
          primer encoded
          ~~~~~~~~~~~~~~~~~~~~~~~~~~~~~~~~~~~~~~~~~~~~~~~~~~~~~~~~~~~~~~~~
          Q   V   Q   L   V   Q   S   G   A   E   V   K   K   P   G   A   S   V   K
  1       CAG GTG CAG CTG GTG CAG TCT GGG GCT GAG GTG AAG AAG CCT GGG GCC TCA GTG AAG V   S   C   K   V   S   G   Y   T   F   T   K   L   S   V   H   W   V   R
 58       GTC TCC TGC AAG GTT TCC GGA TAC ACC TTC ACT AAA TTA TCC GTG CAC TGG GTG CGA
                                                          ~~~~~~~~~~~~~~~~~
                                                                CDR1
          Q   A   P   G   K   G   L   E   W   M   G   S   F   D   P   E   D   G   E
115       CAG GCT CCT GGA AAA GGG CTT GAG TGG ATG GGA AGT TTT GAT CCT GAA GAT GGT GAA
                                                      ~~~~~~~~~~~~~~~~~~~~~~~~~~~~~~
                                                                  CDR2
          T   I   Y   S   Q   R   F   Q   G   R   V   T   M   T   E   D   T   S   T
172       ACA ATC TAC TCA CAG AGG TTC CAG GGC AGA GTC ACC ATG ACC GAG GAC ACA TCT ACA
          ~~~~~~~~~~~~~
          D   T   A   Y   M   E   L   S   S   L   R   S   E   D   T   A   V   Y   Y
229       GAC ACA GCC TAC ATG GAG CTG AGC AGC CTG AGA TCT GAG GAC ACG GCC GTG TAT TAC
                                                          ~~~~~~~~~~~~~~~~~~~~~~~~~~
                                                                      CDR3
          C   A   T   E   G   Q   W   L   V   A   Y   Y   G   M   D   V   W   G   Q
286       TGT GCA ACG GAG GGG CAG TGG CTG GTA GCC TAC TAC GGT ATG GAC GTC TGG GGC CAA
          ~~~~~~~~~~~~~~~~~~~~~~~~~~~~~~~~~~~~~~~~~~~~~~~~~
          G   T   M   V   T   V   S   S
343       GGG ACC ATG GTC ACC GTC TCC TCA
```

Fig. 2B

Anti-SDF-1 1H2 VK
V segment: L18
J segment: JK4

```
    primer encoded
    ~~~~~~~~~~~~~~~
    E   I   V   L   T   Q   S   P   S   S   L   S   A   S   V   G   D   R   V
1   GAA ATT GTG CTC ACC CAG TCT CCA TCC TCC CTG TCT GCA TCT GTA GGA GAC AGA GTC
                                        ~~~~~~~~~~~~~~~~~~~~~~~~~~~~~~~~~~~~~~
                                                        CDR1
    T   I   T   C   R   A   S   Q   S   I   S   S   A   L   A   W   Y   Q   Q
58  ACC ATC ACT TGC CGG GCA AGT CAG AGT ATT AGC AGT GCT TTA GCC TGG TAT CAG CAG
    ~~~~~~~~~~~~~~~~~~~~~~~~~~~~~~~~~~~~~~~~~~~~~~~~~~~~~~~~~~~~~
                                                                     CDR2
    K   P   G   K   A   P   K   L   L   I   Y   D   A   S   S   L   E   S   G
115 AAA CCA GGG AAA GCT CCT AAG CTC CTG ATC TAT GAT GCC TCC AGT TTG GAA AGT GGG
    V   P   S   R   F   S   G   S   G   S   G   T   D   F   T   L   T   I   S
172 GTC CCA TCA AGG TTC AGC GGC AGT GGA TCT GGG ACA GAT TTC ACT CTC ACC ATC AGC
                                                                         ~~~~~
                                                                          CDR3
    S   L   Q   P   E   D   F   A   T   Y   Y   C   Q   Q   F   N   S   Y   P
229 AGC CTG CAG CCT GAA GAT TTT GCA ACT TAT TAC TGT CAA CAG TTT AAT AGT TAC CCG
    ~~~~~~~~~~~~~~~~~~~~~~~~~~~~~~~~~~~~
    CDR3
    L   T   F   G   G   G   T   K   V   E   I   K
286 CTC ACT TTC GGC GGA GGG ACC AAG GTG GAG ATC AAA
```

Fig. 3A

Anti-SDF-1 1C6 VH
V segment: 3-7
D segment: 7-27
J segment: JH6b primer encoded

```
      E   V   Q   L   V   E   S   G   R   G   L   V   Q   P   G   G   S   L   R
  1   GAA GTG CAG CTG GTG GAG TCT GGG AGA GGC TTG GTC CAG CCT GGG GGG TCC CTG AGA
                                                              CDR1
      L   S   C   A   A   S   G   F   T   F   S   S   Y   W   M   S   W   V   R
 58   CTC TCC TGT GCA GCC TCT GGA TTC ACC TTT AGT AGC TAT TGG ATG AGC TGG GTC CGC
                                                      A   N   M   N   Q   D   G   S   E
115   CAG GCT CCA GGG AAA GGG CTG GAG TGG GTG GCC AAC ATG AAT CAA GAT GGA AGT GAG
                                  CDR2
      K   Y   Y   V   D   S   V   K   G   R   F   T   I   S   R   D   N   A   K
172   AAA TAC TAT GTG GAC TCT GTG AAG GGC CGA TTC ACC ATC TCC AGA GAC AAC GCC AAG
      N   S   L   Y   L   Q   M   N   S   L   R   A   E   D   T   A   V   Y   Y
229   AAC TCA CTG TAT CTG CAA ATG AAC AGC CTG AGA GCC GAG GAC ACG GCT GTG TAT TAC
                                              CDR3
      C   A   R   D   L   T   G   P   Y   Y   Y   Y   D   Y   Y   G   M   D   V   W
286   TGT GCG AGG GAT CTA ACT GGG CCA TAT TAC TAT TAC GAC TAC TAC GGT ATG GAC GTC TGG
      G   Q   G   T   T   V   T   V   S   S
343   GGC CAA GGG ACC ACG GTC ACC GTC TCC TCA
```

Fig. 3B

Anti-SDF-1 1C6 VK
V segment: L18
J segment: JK1 primer encoded
~~~~~~~~~~~~~~~

```
      A   I   R   M   T   Q   S   P   S   S   V   S   A   S   V   G   D   R   V
  1   GCC ATC CGG ATG ACC CAG TCT CCA TCT TCC GTG TCT GCA TCT GTA GGA GAC AGA GTC
                                          ~~~~~~~~~~~~~~~~~~~~~~~~~~~
                                                   CDR1
      T   I   T   C   R   A   S   Q   S   I   S   A   L   A   W   Y   Q   Q
 58   ACC ATC ACT TGC CGG GCA AGT CAG AGT ATT AGC GCT TTA GCC TGG TAT CAG CAG
      ~~~~~~~~~~~~~~~~
      T   P   G   K   A   P   K   L   L   I   Y   D   A   S   S   L   E   S   G
115   ACA CCA GGG AAA GCT CCT AAG CTC CTG ATC TAT GAT GCC TCC AGT TTG GAA AGT GGG
                                          ~~~~~~~~~~~~~~~~~~~~~
                                                   CDR2
      V   P   S   R   F   S   G   S   G   S   G   T   D   F   T   L   T   I   S
172   GTC CCA TCA AGG TTC AGC GGC AGT GGA TCT GGG ACA GAT TTC ACT CTC ACC ATC AGC
                                                                              ~~~
                                                                              CDR3
      S   L   Q   P   E   D   F   A   T   Y   Y   C   Q   Q   F   N   S   Y   P
229   AGC CTG CAG CCT GAA GAT TTT GCA ACT TAT TAC TGT CAA CAG TTT AAT AGT TAC CCT
      ~~~~~~~~~~~~~~~~~~~~~~~~~~~~~~~~~~~~~~~~~~~~
                       CDR3
      R   T   F   G   Q   G   T   K   V   E   I   K
286   CGG ACG TTC GGC CAA GGG ACC AAG GTG GAA ATC AAA
```

Fig. 4A

```
Anti-SDF-1 2A5 VH
    V segment:  3-7
    D segment:  7-27
    J segment:  JH6b
```

```
         primer encoded
         ~~~~~~~~~~~~~~~
         Q   V   Q   L   V   Q   S   G   G   G   L   V   Q   P   G   G   S   L   R
   1     CAG GTG CAG CTG GTG CAG TCT GGG GGA GGC TTG GTC CAG CCT GGG GGG TCC CTG AGA
                                                                 CDR1
                                                         ~~~~~~~~~~~~~~~~~~~~~~~~~~
         L   S   C   A   A   S   G   F   T   F   S   S   Y   W   M   S   W   V   R
  58     CTC TCC TGT GCA GCC TCT GGA TTC ACC TTT AGT AGC TAT TGG ATG AGC TGG GTC CGC
         ~~~~~~~~~~~~~~~~~~~~~~~~~~~~~~
         Q   A   P   G   K   G   L   E   W   V   A   N   M   N   Q   D   G   S   E
 115     CAG GCT CCA GGG AAA GGG CTG GAG TGG GTG GCC AAC ATG AAT CAA GAT GGA AGT GAG
                                                 CDR2
                                         ~~~~~~~~~~~~~~~~~~~~~~~~~~~~~~~~~~~~~~~~~~
         K   Y   Y   V   D   S   V   K   G   R   F   T   I   S   R   D   N   A   K
 172     AAA TAC TAT GTG GAC TCT GTG AAG GGC CGA TTC ACC ATC TCC AGA GAC AAC GCC AAG
         ~~~~~
         N   S   L   Y   L   Q   M   N   S   L   R   A   E   D   T   A   V   Y   Y
 229     AAC TCA CTG TAT CTG CAA ATG AAC AGC CTG AGA GCC GAG GAC ACG GCT GTG TAT TAC
                                                         CDR3
                                                 ~~~~~~~~~~~~~~~~~~~~~~~~~~~~~~~~~~
         C   A   R   D   L   T   G   P   Y   Y   Y   Y   D   Y   Y   G   M   D   V   W
 286     TGT GCG AGG GAT CTA ACT GGG CCA TAT TAC TAC TAC GAC TAC TAC GGT ATG GAC GTC TGG
         ~~~~~~~~~~~~~~~~~~~~~~~~~~~~~~~~~~~~~~~~~~~~~~~~~~~~~~~
         G   Q   G   T   T   V   T   V   S   S
 343     GGC CAA GGG ACC ACG GTC ACC GTC TCC TCA
```

Fig. 4B

Anti-SDF-1 2A5 VK
V segment: L18
J segment: JK1

```
     primer encoded
     ~~~~~~~~~~~~~~~~~~~~~~~~~~~~~~~~~~~
     D   I   Q   M   I   Q   S   P   S   S   L   S   A   S   V   G   D   R   V
  1  GAC ATC CAG ATG ATC CAG TCT CCA TCC TCC CTG TCT GCA TCT GTA GGA GAC AGA GTC
                                             ~~~~~~~~~~~~~~~~~~~~~~~~~~~~~~~~~~~
                                                       CDR1
     T   I   T   C   R   A   S   Q   G   I   S   S   A   L   A   W   Y   Q   Q
 58  ACC ATC ACT TGC CGG GCA AGT CAG GGC ATT AGC AGT GCT TTA GCC TGG TAT CAG CAG
     ~~~~~~~~~~~~~~~~~~~~
                                                                      ~~~~~~~~~~
                                                                          CDR2
     K   P   G   K   A   P   K   L   L   I   Y   D   A   S   S   L   E   S   G
115  AAA CCA GGG AAA GCT CCT AAG CTC CTG ATC TAT GAT GCC TCC AGT TTG GAA AGT GGG
     ~~~~~~~~~~~~~~~~~~~~~~~~~~~~~~~~~~~~~~~~~~~
     V   P   S   R   F   S   G   S   G   S   G   T   D   F   T   L   T   I   S
172  GTC CCA TCA AGG TTC AGC GGC AGT GGA TCT GGG ACA GAT TTC ACT CTC ACC ATC AGC
                                                                              ~~
                                                                         CDR3
     S   L   Q   P   E   D   F   A   T   Y   Y   C   Q   Q   F   N   S   Y   P
229  AGC CTG CAG CCT GAA GAT TTT GCA ACT TAT TAC TGT CAA CAG TTT AAT AGT TAC CCT
     ~~~~~~~~~~~~~
       CDR3
     R   T   F   G   Q   G   T   K   V   E   I   K
286  CGG ACG TTC GGC CAA GGG ACC AAG GTG GAA ATC AAA
```

Fig. 5

Anti-SDF-1 1D3 and 1H2 VH region

```
              primer encoded                                          CDR1
1-24 germline Q V Q L V Q S G A E V K K P G A S V K V S C K V S G Y T L T E L S M H W
1D3 VH        E - - - - - - - - - - - - - - - - - - - - - - - - - - - - - K - - - -
1H2 VH        - - - - - - - - - - - - - - - - - - - - - - - - - - - F - K - - V - - -
                                                       CDR2
1-24 germline V R Q A P G K G L E W M G G F D P E D G E T I Y A Q K F Q G R V T M T E
1D3 VH        - - - - - - - - - - - - - S - - - - - - - - - S - R - - - - - - - - - -
1H2 VH        - - - - - - - - - - - - - S - - - - - - - - - S - R - - - - - - - - - -
                                                                           CDR3
1-24 germline D T S T D T A Y M E L S S L R S E D T A V Y Y C A T
1D3 VH        - - - - - - - - - - - - - - - - - - - - - - - - - -  E G Q W L V A - Y Y G
1H2 VH        - - - - - - - - - - - - T - - - - - - - - - - - - -  E G Q W L V A - - - -

MDVWGQGTTVTVSS
JH6b germline M D V W G Q G T T V T V S S
1D3 VH        - - - - - - - - - - - - - -  (JH6b)
1H2 VH        - - - - M - - - - - - - - -  (JH6b)
```

Fig. 6

Anti-SDF-1 1C6 and 2A5 VH region

```
                    primer encoded                              CDR1
3-7 germline    E V Q L V E S G G G L V Q P G G S L R L S C A A S G F T F S S Y W M S W
1C6 VH          - - - - - - - - - - - - - - - - R - - - - - - - - - - - - - - - - - -
2A5 VH          Q - - - Q - - - - - - - - - - - - - - - - - - - - - - - - - - - - - -

CDR2
3-7 germline    V R Q A P G K G L E W V A N I K Q D G S E K Y Y V D S V K G R F T I S R
1C6 VH          - - - - - - - - - - - - - M N - - - - - - - - - - - - - - - - - - - -
2A5 VH          - - - - - - - - - - - - - M N - - - - - - - - - - - - - - - - - - - -

CDR3
3-7 germline    D N A K N S L Y L Q M N S L R A E D T A V Y Y C A R
JH6b germline                                                        Y Y Y Y Y - - D -
1C6 VH          - - - - - - - - - - - - - - - - - - - - - - - - - - D L T G P Y - - - -
2A5 VH          - - - - - - - - - - - - - - - - - - - - - - - - - - D L T G P Y - - D -

CDR3
JH6b germline   Y G M D V W G Q G T T V T V S S   (JH6b)
1C6 VH          - - - - - - - - - - - - - - - -   (JH6b)
2A5 VH          - - - - - - - - - - - - - - - -
```

Fig. 7

Anti-SDF-1 1D3 and 1H2 VK region

```
               primer encoded                              CDR1
L18 germline   A I Q L T Q S P S S L S A S V G D R V T I T C R A S Q G I S S
1D3 VK         E - V - - - - - - - - - - - - - - - - - - - - - - - - - - -
1H2 VK         E - V - - - - - - - - - - - - - - - - - - - - - - - - - - -

CDR2
L18 germline   A L A W Y Q Q K P G K A P K L L I Y D A S S L E S G V P S R F
1D3 VK         - - - - - - - - - - - - - - - - - - - - - - - - - - - - - -
1H2 VK         - - - - - - - - - - - - - - - - - - - - - - - - - - - - - -

CDR3
L18 germline   S G S G S G T D F T L T I S S L Q P E D F A T Y Y C Q Q F N N
1D3 VK         - - - - - - - - - - - - - - - - - - - - - - - - - - - - - S
1H2 VK         - - - - - - - - - - - - - - - - - - - - - - - - - - - - - S L18 germline   Y P
JK4 germline           L T F G G G T K V E I K
1D3 VK         - -     - - - - - - - - - - - -   (JK4)
1H2 VK         - -     - - - - - - - - - - - -   (JK4)
```

Fig. 8

Anti-SDF-1 1C6 and 2A5 VK region

```
                  primer encoded                                    CDR1
L18 germline    A I Q L T Q S P S S L S A S V G D R V T I T C R A S Q G I S S
1C6 VK          - - R M - - - - - - - V - - - - - - - - - - - - - - - - - - -
2A5 VK          D - - M I - - - - - - - - - - - - - - - - - - - - - - - - - -

CDR2
L18 germline    A L A W Y Q Q K P G K A P K L L I Y D A S S L E S G V P S R F
1C6 VK          - - - - - - - - - T - - - - - - - - - - - - - - - - - - - - -
2A5 VK          - - - - - - - - - - - - - - - - - - - - - - - - - - - - - - -

CDR3
L18 germline    S G S G S G T D F T L T I S S L Q P E D F A T Y Y C Q Q F N N
1C6 VK          - - - - - - - - - - - - - - - - - - - - - - - - - - - - - - S
2A5 VK          - - - - - - - - - - - - - - - - - - - - - - - - - - - - - - S L18 germline    Y P
JK1 germline        W T F G Q G T K V E I K
1C6 VK          - -  - - R - - - - - - - -     (JK1)
2A5 VK          - -  - - R - - - - - - - -     (JK1)
```

Fig. 9
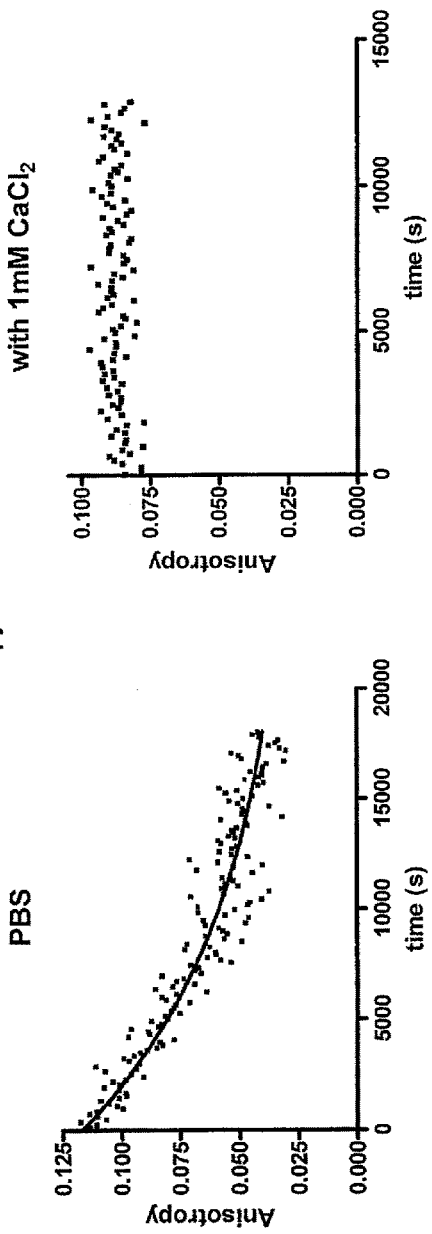
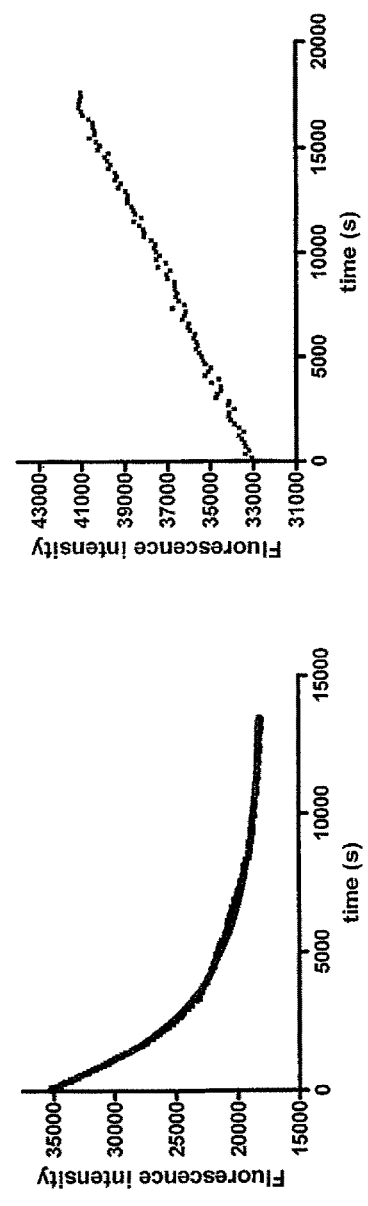

A

B

C

D

E

F

Fig. 14
A
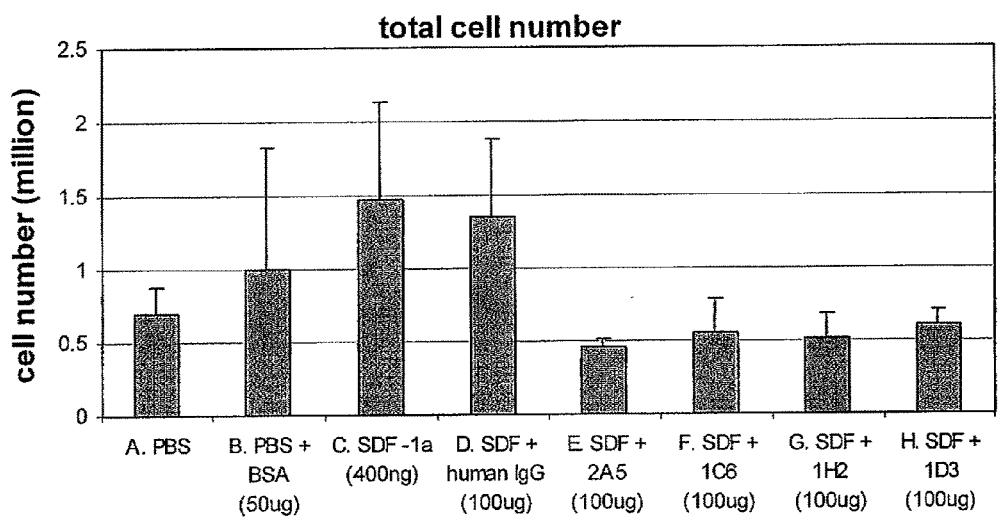
B
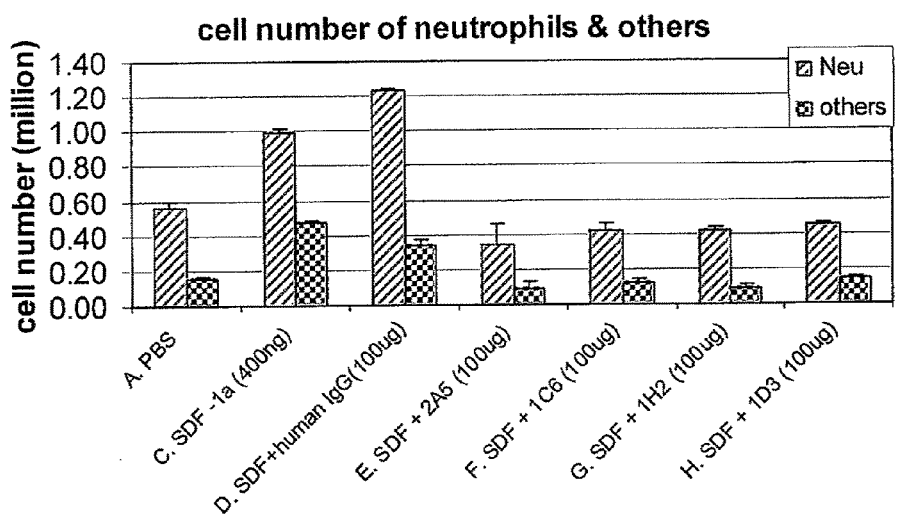

Fig. 15
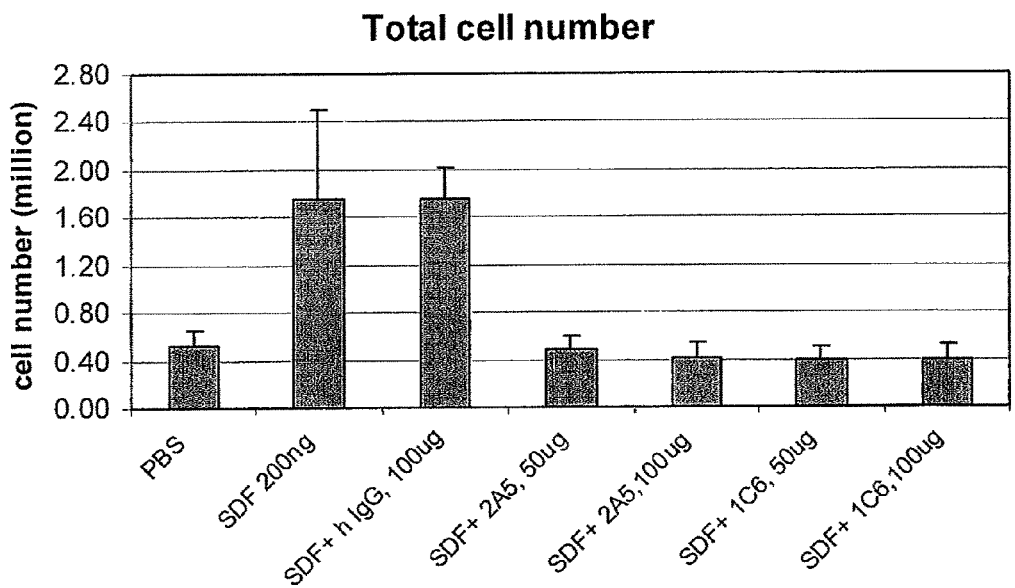
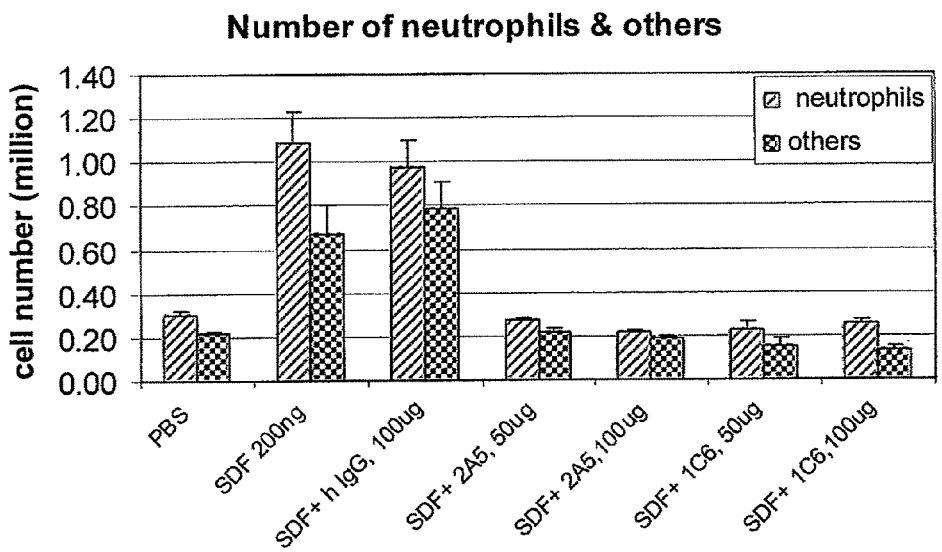

Fig. 16
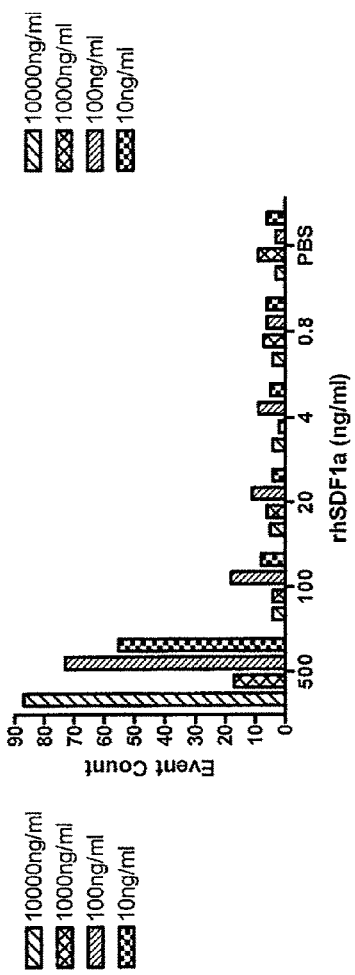
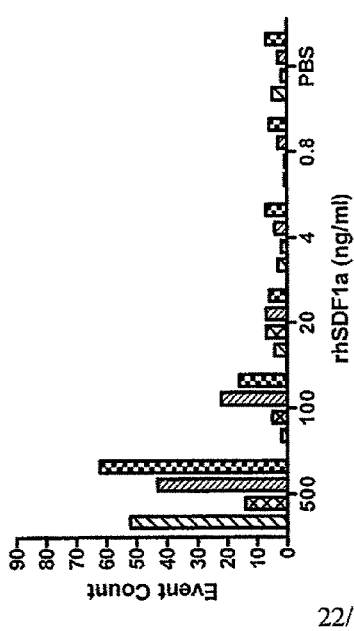
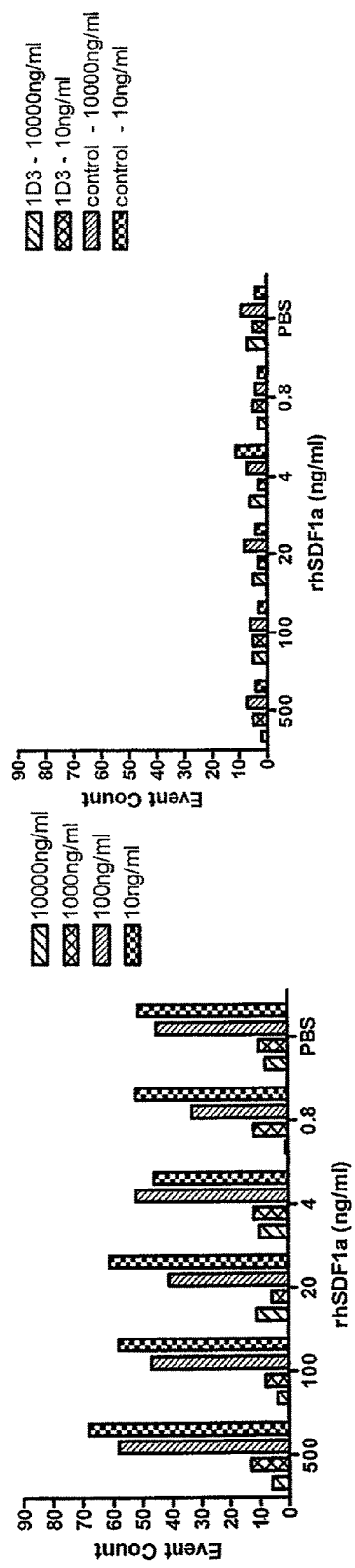

```
                        SEQUENCE LISTING

<160> NUMBER OF SEQ ID NOS: 51

<210> SEQ ID NO 1
<211> LENGTH: 122
<212> TYPE: PRT
<213> ORGANISM: Homo sapiens

<400> SEQUENCE: 1

Glu Val Gln Leu Val Gln Ser Gly Ala Glu Val Lys Lys Pro Gly Ala
  1               5                  10                  15

Ser Val Lys Val Ser Cys Lys Val Ser Gly Tyr Thr Leu Thr Lys Leu
                 20                  25                  30

Ser Val His Trp Val Arg Gln Ala Pro Gly Lys Gly Leu Glu Trp Met
             35                  40                  45

Gly Ser Phe Asp Pro Glu Asp Gly Glu Thr Ile Tyr Ser Gln Arg Phe
         50                  55                  60

Gln Gly Arg Val Thr Met Thr Glu Asp Thr Ser Thr Asp Thr Ala Tyr
 65                  70                  75                  80

Met Glu Leu Thr Ser Leu Arg Ser Glu Asp Thr Ala Val Tyr Tyr Cys
                 85                  90                  95

Ala Thr Glu Gly Gln Trp Leu Val Ala Tyr Tyr Gly Met Asp Val Trp
                100                 105                 110

Gly Gln Gly Thr Thr Val Thr Val Ser Ser
            115                 120

<210> SEQ ID NO 2
<211> LENGTH: 122
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
  1               5                  10                  15

Ser Val Lys Val Ser Cys Lys Val Ser Gly Tyr Thr Phe Thr Lys Leu
                 20                  25                  30
```

```
Ser Val His Trp Val Arg Gln Ala Pro Gly Lys Gly Leu Glu Trp Met
        35                  40                  45

Gly Ser Phe Asp Pro Glu Asp Gly Glu Thr Ile Tyr Ser Gln Arg Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Glu Gly Gln Trp Leu Val Ala Tyr Tyr Gly Met Asp Val Trp
                100                 105                 110

Gly Gln Gly Thr Met Val Thr Val Ser Ser
            115                 120

<210> SEQ ID NO 3
<211> LENGTH: 124
<212> TYPE: PRT
<213> ORGANISM: Homo sapiens

<400> SEQUENCE: 3

Glu Val Gln Leu Val Glu Ser Gly Arg Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Met Ser Trp Val Arg Gln Ala Pro Gly Lys Gly Leu Glu Trp Val
            35                  40                  45

Ala Asn Met Asn Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Thr Gly Pro Tyr Tyr Tyr Asp Tyr Tyr Gly Met Asp
                100                 105                 110

Val Trp Gly Gln Gly Thr Thr Val Thr Val Ser Ser
            115                 120

<210> SEQ ID NO 4
<211> LENGTH: 124
<212> TYPE: PRT
<213> ORGANISM: Homo sapiens

<400> SEQUENCE: 4

Gln Val Gln Leu Val Gln Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Met Ser Trp Val Arg Gln Ala Pro Gly Lys Gly Leu Glu Trp Val
            35                  40                  45

Ala Asn Met Asn Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Thr Gly Pro Tyr Tyr Tyr Asp Tyr Tyr Gly Met Asp
                100                 105                 110

Val Trp Gly Gln Gly Thr Thr Val Thr Val Ser Ser
```

```
              115                 120

<210> SEQ ID NO 5
<211> LENGTH: 107
<212> TYPE: PRT
<213> ORGANISM: Homo sapiens

<400> SEQUENCE: 5

Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
            100                 105

<210> SEQ ID NO 6
<211> LENGTH: 107
<212> TYPE: PRT
<213> ORGANISM: Homo sapiens

<400> SEQUENCE: 6

Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
            100                 105

<210> SEQ ID NO 7
<211> LENGTH: 107
<212> TYPE: PRT
<213> ORGANISM: Homo sapiens

<400> SEQUENCE: 7

Ala Ile Arg Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Thr Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Arg
                 85                  90                  95

Thr Phe Gly Gln Gly Thr Lys Val Glu Ile Lys
            100                 105
```

<210> SEQ ID NO 8
<211> LENGTH: 107
<212> TYPE: PRT
<213> ORGANISM: Homo sapiens

<400> SEQUENCE: 8

```
Asp Ile Gln Met Ile Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Arg
                 85                  90                  95

Thr Phe Gly Gln Gly Thr Lys Val Glu Ile Lys
            100                 105
```

<210> SEQ ID NO 9
<211> LENGTH: 5
<212> TYPE: PRT
<213> ORGANISM: Homo sapiens

<400> SEQUENCE: 9

```
Lys Leu Ser Val His
 1               5
```

<210> SEQ ID NO 10
<211> LENGTH: 5
<212> TYPE: PRT
<213> ORGANISM: Homo sapiens

<400> SEQUENCE: 10

```
Lys Leu Ser Val His
 1               5
```

<210> SEQ ID NO 11
<211> LENGTH: 5
<212> TYPE: PRT
<213> ORGANISM: Homo sapiens

<400> SEQUENCE: 11

```
Ser Tyr Trp Met Ser
 1               5
```

<210> SEQ ID NO 12
<211> LENGTH: 5
<212> TYPE: PRT
<213> ORGANISM: Homo sapiens

<400> SEQUENCE: 12

Ser Tyr Trp Met Ser

<210> SEQ ID NO 13
<211> LENGTH: 17
<212> TYPE: PRT
<213> ORGANISM: Homo sapiens

<400> SEQUENCE: 13

Ser Phe Asp Pro Glu Asp Gly Glu Thr Ile Tyr Ser Gln Arg Phe Gln
 1               5                  10                  15
Gly

<210> SEQ ID NO 14
<211> LENGTH: 17
<212> TYPE: PRT
<213> ORGANISM: Homo sapiens

<400> SEQUENCE: 14

Ser Phe Asp Pro Glu Asp Gly Glu Thr Ile Tyr Ser Gln Arg Phe Gln
 1               5                  10                  15
Gly

<210> SEQ ID NO 15
<211> LENGTH: 17
<212> TYPE: PRT
<213> ORGANISM: Homo sapiens

<400> SEQUENCE: 15

Asn Met Asn Gln Asp Gly Ser Glu Lys Tyr Tyr Val Asp Ser Val Lys
 1               5                  10                  15
Gly

<210> SEQ ID NO 16
<211> LENGTH: 17
<212> TYPE: PRT
<213> ORGANISM: Homo sapiens

<400> SEQUENCE: 16

Asn Met Asn Gln Asp Gly Ser Glu Lys Tyr Tyr Val Asp Ser Val Lys
 1               5                  10                  15
Gly

<210> SEQ ID NO 17
<211> LENGTH: 13
<212> TYPE: PRT
<213> ORGANISM: Homo sapiens

<400> SEQUENCE: 17

Glu Gly Gln Trp Leu Val Ala Tyr Tyr Gly Met Asp Val
 1               5                  10

<210> SEQ ID NO 18
<211> LENGTH: 13
<212> TYPE: PRT
<213> ORGANISM: Homo sapiens

<400> SEQUENCE: 18

Glu Gly Gln Trp Leu Val Ala Tyr Tyr Gly Met Asp Val
 1               5                  10

<210> SEQ ID NO 19
<211> LENGTH: 15
<212> TYPE: PRT

-continued

<213> ORGANISM: Homo sapiens

<400> SEQUENCE: 19

Asp Leu Thr Gly Pro Tyr Tyr Asp Tyr Tyr Gly Met Asp Val
1               5                   10                  15

<210> SEQ ID NO 20
<211> LENGTH: 15
<212> TYPE: PRT
<213> ORGANISM: Homo sapiens

<400> SEQUENCE: 20

Asp Leu Thr Gly Pro Tyr Tyr Asp Tyr Tyr Gly Met Asp Val
1               5                   10                  15

<210> SEQ ID NO 21
<211> LENGTH: 11
<212> TYPE: PRT
<213> ORGANISM: Homo sapiens

<400> SEQUENCE: 21

Arg Ala Ser Gln Gly Ile Ser Ser Ala Leu Ala
1               5                   10

<210> SEQ ID NO 22
<211> LENGTH: 11
<212> TYPE: PRT
<213> ORGANISM: Homo sapiens

<400> SEQUENCE: 22

Arg Ala Ser Gln Gly Ile Ser Ser Ala Leu Ala
1               5                   10

<210> SEQ ID NO 23
<211> LENGTH: 11
<212> TYPE: PRT
<213> ORGANISM: Homo sapiens

<400> SEQUENCE: 23

Arg Ala Ser Gln Gly Ile Ser Ser Ala Leu Ala
1               5                   10

<210> SEQ ID NO 24
<211> LENGTH: 11
<212> TYPE: PRT
<213> ORGANISM: Homo sapiens

<400> SEQUENCE: 24

Arg Ala Ser Gln Gly Ile Ser Ser Ala Leu Ala
1               5                   10

<210> SEQ ID NO 25
<211> LENGTH: 7
<212> TYPE: PRT
<213> ORGANISM: Homo sapiens

<400> SEQUENCE: 25

Asp Ala Ser Ser Leu Glu Ser
1               5

<210> SEQ ID NO 26
<211> LENGTH: 7
<212> TYPE: PRT
<213> ORGANISM: Homo sapiens

<400> SEQUENCE: 26

Asp Ala Ser Ser Leu Glu Ser
1               5

<210> SEQ ID NO 27
<211> LENGTH: 7
<212> TYPE: PRT
<213> ORGANISM: Homo sapiens

<400> SEQUENCE: 27

Asp Ala Ser Ser Leu Glu Ser
1               5

<210> SEQ ID NO 28
<211> LENGTH: 7
<212> TYPE: PRT
<213> ORGANISM: Homo sapiens

<400> SEQUENCE: 28

Asp Ala Ser Ser Leu Glu Ser
1               5

<210> SEQ ID NO 29
<211> LENGTH: 9
<212> TYPE: PRT
<213> ORGANISM: Homo sapiens

<400> SEQUENCE: 29

Gln Gln Phe Asn Ser Tyr Pro Leu Thr
1               5

<210> SEQ ID NO 30
<211> LENGTH: 9
<212> TYPE: PRT
<213> ORGANISM: Homo sapiens

<400> SEQUENCE: 30

Gln Gln Phe Asn Ser Tyr Pro Leu Thr
1               5

<210> SEQ ID NO 31
<211> LENGTH: 9
<212> TYPE: PRT
<213> ORGANISM: Homo sapiens

<400> SEQUENCE: 31

Gln Gln Phe Asn Ser Tyr Pro Arg Thr
1               5

<210> SEQ ID NO 32
<211> LENGTH: 9
<212> TYPE: PRT
<213> ORGANISM: Homo sapiens

<400> SEQUENCE: 32

Gln Gln Phe Asn Ser Tyr Pro Arg Thr
1               5

<210> SEQ ID NO 33
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 33

```
gag gtg cag ctg gtg cag tct ggg gct gag gtg aag aag cct ggg gcc      48
Glu Val Gln Leu Val Gln Ser Gly Ala Glu Val Lys Lys Pro Gly Ala
 1               5                  10                  15 tca gtg aag gtc tcc tgc aag gtt tcc gga tac acc ctc act aaa tta      96
Ser Val Lys Val Ser Cys Lys Val Ser Gly Tyr Thr Leu Thr Lys Leu
             20                  25                  30 tcc gtg cac tgg gtg cga cag gct cct gga aaa ggg ctt gag tgg atg     144
Ser Val His Trp Val Arg Gln Ala Pro Gly Lys Gly Leu Glu Trp Met
         35                  40                  45 gga agt ttt gat cct gaa gat ggt gaa aca atc tac tca cag agg ttc     192
Gly Ser Phe Asp Pro Glu Asp Gly Glu Thr Ile Tyr Ser Gln Arg Phe
     50                  55                  60 cag ggc aga gtc acc atg acc gag gac aca tct aca gac aca gcc tac     240
Gln Gly Arg Val Thr Met Thr Glu Asp Thr Ser Thr Asp Thr Ala Tyr
 65                  70                  75                  80 atg gag ctg acc agc ctg aga tct gag gac acg gcc gtg tat tac tgt     288
Met Glu Leu Thr Ser Leu Arg Ser Glu Asp Thr Ala Val Tyr Tyr Cys
                 85                  90                  95 gca acg gag ggg cag tgg ctg gta gcc tac tac ggt atg gac gtc tgg     336
Ala Thr Glu Gly Gln Trp Leu Val Ala Tyr Tyr Gly Met Asp Val Trp
             100                 105                 110 ggc caa ggg acc acg gtc acc gtc tcc tca                             366
Gly Gln Gly Thr Thr Val Thr Val Ser Ser
         115                 120

<210> SEQ ID NO 34
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 34 cag gtg cag ctg gtg cag tct ggg gct gag gtg aag aag cct ggg gcc      48
Gln Val Gln Leu Val Gln Ser Gly Ala Glu Val Lys Lys Pro Gly Ala
 1               5                  10                  15 tca gtg aag gtc tcc tgc aag gtt tcc gga tac acc ttc act aaa tta      96
Ser Val Lys Val Ser Cys Lys Val Ser Gly Tyr Thr Phe Thr Lys Leu
             20                  25                  30 tcc gtg cac tgg gtg cga cag gct cct gga aaa ggg ctt gag tgg atg     144
Ser Val His Trp Val Arg Gln Ala Pro Gly Lys Gly Leu Glu Trp Met
         35                  40                  45 gga agt ttt gat cct gaa gat ggt gaa aca atc tac tca cag agg ttc     192
Gly Ser Phe Asp Pro Glu Asp Gly Glu Thr Ile Tyr Ser Gln Arg Phe
     50                  55                  60 cag ggc aga gtc acc atg acc gag gac aca tct aca gac aca gcc tac     240
Gln Gly Arg Val Thr Met Thr Glu Asp Thr Ser Thr Asp Thr Ala Tyr
 65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                 85                  90                  95 gca acg gag ggg cag tgg ctg gta gcc tac tac ggt atg gac gtc tgg     336
Ala Thr Glu Gly Gln Trp Leu Val Ala Tyr Tyr Gly Met Asp Val Trp
             100                 105                 110 ggc caa ggg acc atg gtc acc gtc tcc tca                             366
Gly Gln Gly Thr Met Val Thr Val Ser Ser
         115                 120

<210> SEQ ID NO 35
<211> LENGTH: 372
<212> TYPE: DNA
```

```
<213> ORGANISM: Homo sapiens
<220> FEATURE:
<221> NAME/KEY: CDS
<222> LOCATION: (1)..(372)

<400> SEQUENCE: 35 gaa gtg cag ctg gtg gag tct ggg aga ggc ttg gtc cag cct ggg ggg      48
Glu Val Gln Leu Val Glu Ser Gly Arg Gly Leu Val Gln Pro Gly Gly
 1               5                  10                  15 tcc ctg aga ctc tcc tgt gca gcc tct gga ttc acc ttt agt agc tat      96
Ser Leu Arg Leu Ser Cys Ala Ala Ser Gly Phe Thr Phe Ser Ser Tyr
             20                  25                  30 tgg atg agc tgg gtc cgc cag gct cca ggg aaa ggg ctg gag tgg gtg     144
Trp Met Ser Trp Val Arg Gln Ala Pro Gly Lys Gly Leu Glu Trp Val
         35                  40                  45 gcc aac atg aat caa gat gga agt gag aaa tac tat gtg gac tct gtg     192
Ala Asn Met Asn Gln Asp Gly Ser Glu Lys Tyr Tyr Val Asp Ser Val
     50                  55                  60 aag ggc cga ttc acc atc tcc aga gac aac gcc aag aac tca ctg tat     240
Lys Gly Arg Phe Thr Ile Ser Arg Asp Asn Ala Lys Asn Ser Leu Tyr
 65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                 85                  90                  95 gcg agg gat cta act ggg cca tat tac tat gac tac tac ggt atg gac     336
Ala Arg Asp Leu Thr Gly Pro Tyr Tyr Tyr Asp Tyr Tyr Gly Met Asp
            100                 105                 110 gtc tgg ggc caa ggg acc acg gtc acc gtc tcc tca                     372
Val Trp Gly Gln Gly Thr Thr Val Thr Val Ser Ser
        115                 120

<210> SEQ ID NO 36
<211> LENGTH: 372
<212> TYPE: DNA
<213> ORGANISM: Homo sapiens
<220> FEATURE:
<221> NAME/KEY: CDS
<222> LOCATION: (1)..(372)

<400> SEQUENCE: 36 cag gtg cag ctg gtg cag tct ggg gga ggc ttg gtc cag cct ggg ggg      48
Gln Val Gln Leu Val Gln Ser Gly Gly Gly Leu Val Gln Pro Gly Gly
 1               5                  10                  15 tcc ctg aga ctc tcc tgt gca gcc tct gga ttc acc ttt agt agc tat      96
Ser Leu Arg Leu Ser Cys Ala Ala Ser Gly Phe Thr Phe Ser Ser Tyr
             20                  25                  30 tgg atg agc tgg gtc cgc cag gct cca ggg aaa ggg ctg gag tgg gtg     144
Trp Met Ser Trp Val Arg Gln Ala Pro Gly Lys Gly Leu Glu Trp Val
         35                  40                  45 gcc aac atg aat caa gat gga agt gag aaa tac tat gtg gac tct gtg     192
Ala Asn Met Asn Gln Asp Gly Ser Glu Lys Tyr Tyr Val Asp Ser Val
     50                  55                  60 aag ggc cga ttc acc atc tcc aga gac aac gcc aag aac tca ctg tat     240
Lys Gly Arg Phe Thr Ile Ser Arg Asp Asn Ala Lys Asn Ser Leu Tyr
 65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                 85                  90                  95 gcg agg gat cta act ggg cca tat tac tat gac tac tac ggt atg gac     336
Ala Arg Asp Leu Thr Gly Pro Tyr Tyr Tyr Asp Tyr Tyr Gly Met Asp
            100                 105                 110 gtc tgg ggc caa ggg acc acg gtc acc gtc tcc tca                     372
Val Trp Gly Gln Gly Thr Thr Val Thr Val Ser Ser
        115                 120
```

<210> SEQ ID NO 37
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 37

```
gaa att gtg ctc acc cag tct cca tcc tcc ctg tct gca tct gta gga      48
Glu Ile Val Leu Thr Gln Ser Pro Ser Ser Leu Ser Ala Ser Val Gly
  1               5                  10                  15 gac aga gtc acc atc act tgc cgg gca agt cag ggc att agc agt gct      96
Asp Arg Val Thr Ile Thr Cys Arg Ala Ser Gln Gly Ile Ser Ser Ala
             20                  25                  30 tta gcc tgg tat cag cag aaa cca ggg aaa gct cct aag ctc ctg atc     144
Leu Ala Trp Tyr Gln Gln Lys Pro Gly Lys Ala Pro Lys Leu Leu Ile
         35                  40                  45 tat gat gcc tcc agt ttg gaa agt ggg gtc cca tca agg ttc agc ggc     192
Tyr Asp Ala Ser Ser Leu Glu Ser Gly Val Pro Ser Arg Phe Ser Gly
     50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
 65                  70                  75                  80 gaa gat ttt gca act tat tac tgt caa cag ttt aat agt tac ccg ctc     288
Glu Asp Phe Ala Thr Tyr Tyr Cys Gln Gln Phe Asn Ser Tyr Pro Leu
                 85                  90                  95 act ttc ggc gga ggg acc aag gtg gag atc aaa                         321
Thr Phe Gly Gly Gly Thr Lys Val Glu Ile Lys
            100                 105
```

<210> SEQ ID NO 38
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 38

```
gaa att gtg ctc acc cag tct cca tcc tcc ctg tct gca tct gta gga      48
Glu Ile Val Leu Thr Gln Ser Pro Ser Ser Leu Ser Ala Ser Val Gly
  1               5                  10                  15 gac aga gtc acc atc act tgc cgg gca agt cag ggc att agc agt gct      96
Asp Arg Val Thr Ile Thr Cys Arg Ala Ser Gln Gly Ile Ser Ser Ala
             20                  25                  30 tta gcc tgg tat cag cag aaa cca ggg aaa gct cct aag ctc ctg atc     144
Leu Ala Trp Tyr Gln Gln Lys Pro Gly Lys Ala Pro Lys Leu Leu Ile
         35                  40                  45 tat gat gcc tcc agt ttg gaa agt ggg gtc cca tca agg ttc agc ggc     192
Tyr Asp Ala Ser Ser Leu Glu Ser Gly Val Pro Ser Arg Phe Ser Gly
     50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
 65                  70                  75                  80 gaa gat ttt gca act tat tac tgt caa cag ttt aat agt tac ccg ctc     288
Glu Asp Phe Ala Thr Tyr Tyr Cys Gln Gln Phe Asn Ser Tyr Pro Leu
                 85                  90                  95 act ttc ggc gga ggg acc aag gtg gag atc aaa                         321
Thr Phe Gly Gly Gly Thr Lys Val Glu Ile Lys
            100                 105
```

<210> SEQ ID NO 39
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 39

```
gcc atc cgg atg acc cag tct cca tct tcc gtg tct gca tct gta gga    48
Ala Ile Arg Met Thr Gln Ser Pro Ser Ser Val Ser Ala Ser Val Gly
 1               5                  10                  15 gac aga gtc acc atc act tgc cgg gca agt cag ggc att agc agt gct    96
Asp Arg Val Thr Ile Thr Cys Arg Ala Ser Gln Gly Ile Ser Ser Ala
             20                  25                  30 tta gcc tgg tat cag cag aca cca ggg aaa gct cct aag ctc ctg atc   144
Leu Ala Trp Tyr Gln Gln Thr Pro Gly Lys Ala Pro Lys Leu Leu Ile
         35                  40                  45 tat gat gcc tcc agt ttg gaa agt ggg gtc cca tca agg ttc agc ggc   192
Tyr Asp Ala Ser Ser Leu Glu Ser Gly Val Pro Ser Arg Phe Ser Gly
     50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
 65                  70                  75                  80 gaa gat ttt gca act tat tac tgt caa cag ttt aat agt tac cct cgg   288
Glu Asp Phe Ala Thr Tyr Tyr Cys Gln Gln Phe Asn Ser Tyr Pro Arg
                 85                  90                  95 acg ttc ggc caa ggg acc aag gtg gaa atc aaa                       321
Thr Phe Gly Gln Gly Thr Lys Val Glu Ile Lys
            100                 105
```

<210> SEQ ID NO 40
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 40

```
gac atc cag atg atc cag tct cca tcc tcc ctg tct gca tct gta gga    48
Asp Ile Gln Met Ile Gln Ser Pro Ser Ser Leu Ser Ala Ser Val Gly
 1               5                  10                  15 gac aga gtc acc atc act tgc cgg gca agt cag ggc att agc agt gct    96
Asp Arg Val Thr Ile Thr Cys Arg Ala Ser Gln Gly Ile Ser Ser Ala
             20                  25                  30 tta gcc tgg tat cag cag aaa cca ggg aaa gct cct aag ctc ctg atc   144
Leu Ala Trp Tyr Gln Gln Lys Pro Gly Lys Ala Pro Lys Leu Leu Ile
         35                  40                  45 tat gat gcc tcc agt ttg gaa agt ggg gtc cca tca agg ttc agc ggc   192
Tyr Asp Ala Ser Ser Leu Glu Ser Gly Val Pro Ser Arg Phe Ser Gly
     50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
 65                  70                  75                  80 gaa gat ttt gca act tat tac tgt caa cag ttt aat agt tac cct cgg   288
Glu Asp Phe Ala Thr Tyr Tyr Cys Gln Gln Phe Asn Ser Tyr Pro Arg
                 85                  90                  95 acg ttc ggc caa ggg acc aag gtg gaa atc aaa                       321
Thr Phe Gly Gln Gly Thr Lys Val Glu Ile Lys
            100                 105
```

<210> SEQ ID NO 41

<211> LENGTH: 98
<212> TYPE: PRT
<213> ORGANISM: Homo sapiens

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 42
<211> LENGTH: 98
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 43
<211> LENGTH: 95
<212> TYPE: PRT
<213> ORGANISM: Homo sapiens

<400> SEQUENCE: 43

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro
                85                  90                  95

-continued

<210> SEQ ID NO 44
<211> LENGTH: 89
<212> TYPE: PRT
<213> ORGANISM: Homo sapiens

<400> SEQUENCE: 44

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 45
<211> LENGTH: 93
<212> TYPE: PRT
<213> ORGANISM: Homo sapiens

<400> SEQUENCE: 45

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 46
<211> LENGTH: 119
<212> TYPE: PRT
<213> ORGANISM: Homo sapiens

<400> SEQUENCE: 46

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Arg Arg Glu Glu Lys Val
                85                  90                  95

Gly Lys Lys Glu Lys Ile Gly Lys Lys Arg Gln Lys Lys Arg Lys
            100                 105                 110

Ala Ala Gln Lys Arg Lys Asn
        115

<210> SEQ ID NO 47
<211> LENGTH: 17
<212> TYPE: PRT
<213> ORGANISM: Homo sapiens

<400> SEQUENCE: 47

Tyr Tyr Gly Met Asp Val Trp Gly Gln Gly Thr Thr Val Thr Val Ser
1               5                   10                  15

Ser

<210> SEQ ID NO 48
<211> LENGTH: 20
<212> TYPE: PRT
<213> ORGANISM: Homo sapiens

<400> SEQUENCE: 48

Tyr Tyr Tyr Tyr Tyr Gly Met Asp Val Trp Gly Gln Gly Thr Thr Val
1               5                   10                  15

Thr Val Ser Ser
            20

<210> SEQ ID NO 49
<211> LENGTH: 12
<212> TYPE: PRT
<213> ORGANISM: Homo sapiens

<400> SEQUENCE: 49

Leu Thr Phe Gly Gly Gly Thr Lys Val Glu Ile Lys
1               5                   10

<210> SEQ ID NO 50
<211> LENGTH: 12
<212> TYPE: PRT
<213> ORGANISM: Homo sapiens

<400> SEQUENCE: 50

Trp Thr Phe Gly Gln Gly Thr Lys Val Glu Ile Lys
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Synthetic construct

<400> SEQUENCE: 51

Gly Gly Gly Gly Ser Gly Gly Gly Gly Ser Gly Gly Gly Gly Ser
1               5                   10                  15

MONOCLONAL ANTIBODIES AGAINST STROMAL DERIVED FACTOR-1 (SDF-1)

BACKGROUND OF THE INVENTION

Chemokines are secreted proteins that are involved in the migration of leukocyte subsets to sites of inflammation, lymphopoiesis, angiogenesis and lymphoid organ development (Nelson and Krensky (2001) *Immunity* 14:377-86; Campbell et al. (2003) *Immunol Rev* 195:58-71; Moser et al. (2004) *Trends Immunol* 25:75-84; Moriguchi et al. (2005) *J Biol Chem* 280:17408-14). Chemokines, through their action in inducing cellular chemotactic responses, play a role in various inflammatory and infectious diseases. The two main subfamilies are distinguished by the position of the first two cysteines, either separated by one amino acid (CXC chemokines) or adjacent (CC chemokines) (Zlotnik and Yoshie (2000) *Immunity* 12:121-7; Loetscher and Clark-Lewis (2001) *J Leukocyte Biol* 69:881-4). Chemokines mediate their function by binding to seven transmembrane G protein-coupled receptors (Murphy et at (2000) *Pharmacol Rev* 52:145-76).

The chemokine Stromal cell-Derived Factor 1 (SDF-1/CXCL12) is the only known natural ligand for the receptor CXCR4. Recent reports suggest that SDF-1 may serve as a ligand for a second receptor, RDC1 (CXCR7) (Balabanian et al. (2005) *J Biol Chem* 280:35760-35766). CXCR4 is widely expressed on both hematopoetic and non-hempatopoetic cell and is found to be expressed on certain tumor cells. It has been suggested that SDF-1 plays a role in directing metastasis of CXCR4+ tumor cells to organs such as lymph node, lung, liver and bone that highly express SDF-1 (Kucia et at (2005) *Stem Cells* 23:879-894). Additional studies have shown that mesenchymal or marrow-derived stromal cells within the tumor microenvironment constitutively secrete SDF-1 (Burger and Kipps 2005).

Murine SDF-1 knockout models show that SDF-1 is critical for colonization of bone marrow by fetal liver derived hematopoietic stem cells during embryogenesis, retention of these cells in adult life, blood vessel formation in the gastrointestinal tract, cardiac ventricular septum formation and cerebellar differentiation (Nagasawa et al. (1996) *Nature* 382:635-8; Ma et al. (1999) *Immunity* 10:463-71; You et al. (1998) *Nature* 393:595-9). SDF-1 has also been suggested to be involved in activation of both Jak and Stat kinases (Vila-Coro et al. (1999) FASEB J13:1699-1710; Zhang et al. (2001) *Blood* 97:3342-8). Also, in diabetics with proliferative diabetic retinopathy, SDF-1 levels were shown to be increased locally in the eye (Butler et al. (2005) *J Clin Invest* 115:86-93).

SUMMARY OF THE INVENTION

The present invention provides isolated monoclonal antibodies, in particular human monoclonal antibodies, that bind to SDF-1 and that exhibit numerous desirable properties. These properties include high affinity binding to human SDF-1, In one aspect, the invention pertains to an isolated monoclonal antibody, or an antigen-binding portion thereof, wherein the antibody:

(a) binds to human SDF-1 with a $K_D$ of $1\times10^{-7}$ M or less; and (b) binds to native human SDF-1 by an immunoprecipitation assay.

Preferably the antibody is a human antibody, although in alternative embodiments the antibody can be a murine antibody, a chimeric antibody or humanized antibody.

In one embodiment, the antibody binds to human SDF-1 with a $K_D$ of $5\times10^{-8}$ M or less, binds to human SDF-1 with a $K_D$ of $2\times10^{-8}$ M or less, binds to human SDF-1 with a $K_D$ of $1\times10^{-8}$ M or less, binds to human SDF-1 with a $K_D$ of $5\times10^{-9}$ M or less, binds to human SDF-1 with a $K_D$ of $4\times10^{-9}$ M or less, binds to human SDF-1 with a $K_D$ of $3\times10^{-9}$ M or less, or binds to human SDF-1 with a $K_D$ of $2\times10^{-9}$ M or less.

In another embodiment, the invention provides an isolated monoclonal antibody, or antigen binding portion thereof, wherein the antibody cross-competes for binding to SDF-1 with a reference antibody comprising:

(a) a heavy chain variable region comprising an amino acid sequence selected from the group consisting of SEQ ID NOs: 1, 2, 3 and 4; and (b) a light chain variable region comprising an amino acid sequence selected from the group consisting of SEQ ID NOs: 5, 6, 7 and 8.

In various embodiments, the reference antibody comprises:

(a) a heavy chain variable region comprising the amino acid sequence of SEQ ID NO:1; and (b) a light chain variable region comprising the amino acid sequence of SEQ ID NO:5; or the reference antibody comprises:

(a) a heavy chain variable region comprising the amino acid sequence of SEQ ID NO:2; and (b) a light chain variable region comprising the amino acid sequence of SEQ ID NO:6; or the reference antibody comprises:

(a) a heavy chain variable region comprising the amino acid sequence of SEQ ID NO:3; and (b) a light chain variable region comprising the amino acid sequence of SEQ ID NO:7; or the reference antibody comprises:

(a) a heavy chain variable region comprising the amino acid sequence of SEQ ID NO:4; and (b) a light chain variable region comprising the amino acid sequence of SEQ ID NO:8.

In another aspect, the invention pertains to an isolated monoclonal antibody, or an antigen-binding portion thereof, comprising a heavy chain variable region that is the product of or derived from a human $V_H$1-24 gene, wherein the antibody specifically binds SDF-1. The invention also provides an isolated monoclonal antibody, or an antigen-binding portion thereof, comprising a heavy chain variable region that is the product of or derived from a human $V_H$3-7 gene, wherein the antibody specifically binds SDF-1. The invention still further provides an isolated monoclonal antibody, or an antigen-binding portion thereof, comprising a light chain variable region that is the product of or derived from a human $V_K$ L18 gene, wherein the antibody specifically binds SDF-1.

In a preferred embodiment, the invention provides an isolated monoclonal antibody, or an antigen-binding portion thereof, comprising:

(a) a heavy chain variable region of a human $V_H$1-24 or 3-7 gene; and (b) a light chain variable region of a human $V_K$ L18 gene; wherein the antibody specifically binds to SDF-1.

In a preferred embodiment, the antibody comprises a heavy chain variable region of a human $V_H$1-24 gene and a light chain variable region of a human $V_K$ L18 gene. In another preferred embodiment, the antibody comprises a heavy chain variable region of a human $V_H$ 3-7 gene and a light chain variable region of a human $V_K$ L18 gene.

In another aspect, the invention provides an isolated monoclonal antibody, or antigen binding portion thereof, comprising:

a heavy chain variable region that comprises CDR1, CDR2, and CDR3 sequences; and a light chain variable region that comprises CDR1, CDR2, and CDR3 sequences, wherein:

(a) the heavy chain variable region CDR3 sequence comprises an amino acid sequence selected from the group consisting of amino acid sequences of SEQ ID NOs:17, 18, 19 and 20, and conservative modifications thereof;

(b) the light chain variable region CDR3 sequence comprises an amino acid sequence selected from the group consisting of amino acid sequence of SEQ ID NOs:29, 30, 31 and 32, and conservative modifications thereof;

(c) the antibody binds to human SDF-1 with a $K_D$ of $1\times10^{-7}$ M or less;

(d) binds to native human SDF-1 by an immunoprecipitation assay.

Preferably, the heavy chain variable region CDR2 sequence comprises an amino acid sequence selected from the group consisting of amino acid sequences of SEQ ID NOs:13, 14, and 16, and conservative modifications thereof; and the light chain variable region CDR2 sequence comprises an amino acid sequence selected from the group consisting of amino acid sequences of SEQ ID NOs:25, 26, 27 and 28, and conservative modifications thereof. Preferably, the heavy chain variable region CDR1 sequence comprises an amino acid sequence selected from the group consisting of amino acid sequences of SEQ ID NOs:9, 10, 11 and 12, and conservative modifications thereof; and the light chain variable region CDR1 sequence comprises an amino acid sequence selected from the group consisting of amino acid sequences of SEQ ID NOs:21, 22, 23 and 24, and conservative modifications thereof.

A preferred combination comprises:

(a) a heavy chain variable region CDR1 comprising SEQ ID NO:9;

(b) a heavy chain variable region CDR2 comprising SEQ ID NO:13;

(c) a heavy chain variable region CDR3 comprising SEQ ID NO:17;

(d) a light chain variable region CDR1 comprising SEQ ID NO:21;

(e) a light chain variable region CDR2 comprising SEQ ID NO:25; and (f) a light chain variable region CDR3 comprising SEQ ID NO:29.

Another preferred combination comprises:

(a) a heavy chain variable region CDR1 comprising SEQ ID NO:10;

(b) a heavy chain variable region CDR2 comprising SEQ ID NO:14;

(c) a heavy chain variable region CDR3 comprising SEQ ID NO:18;

(d) a light chain variable region CDR1 comprising SEQ ID NO:22;

(e) a light chain variable region CDR2 comprising SEQ ID NO:26; and (f) a light chain variable region CDR3 comprising SEQ ID NO:30.

Another preferred combination comprises:

(a) a heavy chain variable region CDR1 comprising SEQ ID NO:11;

(b) a heavy chain variable region CDR2 comprising SEQ ID NO:15;

(c) a heavy chain variable region CDR3 comprising SEQ ID NO:19;

(d) a light chain variable region CDR1 comprising SEQ ID NO:23;

(e) a light chain variable region CDR2 comprising SEQ ID NO:27; and (f) a light chain variable region CDR3 comprising SEQ ID NO:31.

Another preferred combination comprises:

(a) a heavy chain variable region CDR1 comprising SEQ ID NO:12;

(b) a heavy chain variable region CDR2 comprising SEQ ID NO:16;

(c) a heavy chain variable region CDR3 comprising SEQ ID NO:20;

(d) a light chain variable region CDR1 comprising SEQ ID NO:24;

(e) a light chain variable region CDR2 comprising SEQ ID NO:28; and (f) a light chain variable region CDR3 comprising SEQ ID NO:32.

Other preferred antibodies of the invention, or antigen binding portions thereof comprise:

(a) a heavy chain variable region comprising an amino acid sequence selected from the group consisting of SEQ ID NOs: 1, 2, 3 and 4; and (b) a light chain variable region comprising an amino acid sequence selected from the group consisting of SEQ ID NOs: 5, 6, 7 and 8;

wherein the antibody specifically binds SDF-1.

A preferred combination comprises:

(a) a heavy chain variable region comprising the amino acid sequence of SEQ ID NO:1; and (b) a light chain variable region comprising the amino acid sequence of SEQ ID NO:5.

Another preferred combination comprises:

(a) a heavy chain variable region comprising the amino acid sequence of SEQ ID NO:2; and (b) a light chain variable region comprising the amino acid sequence of SEQ ID NO:6.

Another preferred combination comprises:

(a) a heavy chain variable region comprising the amino acid sequence of SEQ ID NO:3; and (b) a light chain variable region comprising the amino acid sequence of SEQ ID NO:7.

Another preferred combination comprises:

(a) a heavy chain variable region comprising the amino acid sequence of SEQ ID NO:4; and (b) a light chain variable region comprising the amino acid sequence of SEQ ID NO:8.

In another aspect of the invention, antibodies, or antigen-binding portions thereof, are provided that compete for binding to SDF-1 with any of the aforementioned antibodies.

The antibodies of the invention can be, for example, full-length antibodies, for example of an IgG1, IgG2 or IgG4 isotype. Alternatively, the antibodies can be antibody fragments, such as Fab, Fab' or Fab'2 fragments, or single chain antibodies.

The invention also provides an immunoconjugate comprising an antibody of the invention, or antigen-binding portion thereof, linked to a therapeutic agent, such as a cytotoxin or a radioactive isotope. The invention also provides a bispecific molecule comprising an antibody, or antigen-binding portion thereof, of the invention, linked to a second functional moiety having a different binding specificity than said antibody, or antigen binding portion thereof.

Compositions comprising an antibody, or antigen-binding portion thereof, or immunoconjugate or bispecific molecule of the invention and a pharmaceutically acceptable carrier are also provided.

Nucleic acid molecules encoding the antibodies, or antigen-binding portions thereof, of the invention are also encompassed by the invention, as well as expression vectors comprising such nucleic acids and host cells comprising such expression vectors.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO:33) and amino acid sequence (SEQ ID NO:1) of the heavy chain variable region of the 1D3 human monoclonal antibody. The CDR1 (SEQ ID NO:9), CDR2 (SEQ ID NO:13) and CDR3 (SEQ ID NO:17) regions are delineated and the V, D and J germline derivations are indicated.

FIG. 1B shows the nucleotide sequence (SEQ ID NO:37) and amino acid sequence (SEQ ID NO:5) of the light chain variable region of the 1D3 human monoclonal antibody. The CDR1 (SEQ ID NO:21), CDR2 (SEQ ID NO:25) and CDR3 (SEQ ID NO:29) regions are delineated and the V and J germline derivations are indicated.

FIG. 2A shows the nucleotide sequence (SEQ ID NO:34) and amino acid sequence (SEQ ID NO:2) of the heavy chain variable region of the 1H2 human monoclonal antibody. The CDR1 (SEQ ID NO:10), CDR2 (SEQ ID NO:14) and CDR3 (SEQ ID NO:18) regions are delineated and the V, D and J germline derivations are indicated.

FIG. 2B shows the nucleotide sequence (SEQ ID NO:38) and amino acid sequence (SEQ ID NO:6) of the light chain variable region of the 1H2 human monoclonal antibody. The CDR1 (SEQ ID NO:22), CDR2 (SEQ ID NO:26) and CDR3 (SEQ ID NO:30) regions are delineated and the V and J germline derivations are indicated.

FIG. 3A shows the nucleotide sequence (SEQ ID NO:35) and amino acid sequence (SEQ ID NO:3) of the heavy chain variable region of the 1C6 human monoclonal antibody. The CDR1 (SEQ ID NO:11), CDR2 (SEQ ID NO:15) and CDR3 (SEQ ID NO:19) regions are delineated and the V, D and J germline derivations are indicated.

FIG. 3B shows the nucleotide sequence (SEQ ID NO:39) and amino acid sequence (SEQ ID NO:7) of the light chain variable region of the 1C6 human monoclonal antibody. The CDR1 (SEQ ID NO:23), CDR2 (SEQ ID NO:27) and CDR3 (SEQ ID NO:31) regions are delineated and the V and J germline derivations are indicated.

FIG. 4A shows the nucleotide sequence (SEQ ID NO:36) and amino acid sequence (SEQ ID NO:4) of the heavy chain variable region of the 2A5 human monoclonal antibody. The CDR1 (SEQ ID NO:12), CDR2 (SEQ ID NO:16) and CDR3 (SEQ ID NO:20) regions are delineated and the V, D and J germline derivations are indicated.

FIG. 4B shows the nucleotide sequence (SEQ ID NO:40) and amino acid sequence (SEQ ID NO:8) of the light chain variable region of the 2A5 human monoclonal antibody. The CDR1 (SEQ ID NO:24), CDR2 (SEQ ID NO:28) and CDR3 (SEQ ID NO:32) regions are delineated and the V and J germline derivations are indicated.

FIG. 5 shows the alignment of the amino acid sequence of the heavy chain variable region of 1D3 (SEQ ID NO: 1) and 1H2 (SEQ ID NO: 2) with the human germline $V_H 1$-24 amino acid sequence (SEQ ID NO:41). The JH6b sequence shown is SEQ ID NO: 47.

FIG. 6 shows the alignment of the amino acid sequence of the heavy chain variable region of 1C6 (SEQ ID NO: 3) and 2A5 (SEQ ID NO: 4) with the human germline $V_H 3$-7 amino acid sequences (SEQ ID NO:42). The JH6b sequence shown is SEQ ID NO: 48.

FIG. 7 shows the alignment of the amino acid sequence of the light chain variable region of 1D3 (SEQ ID NO: 5) and 1H2 (SEQ ID NO: 6) with the human germline $V_k L18$ amino acid sequence (SEQ ID NO:43). The JK4 sequence shown is SEQ ID NO: 49.

FIG. 8 shows the alignment of the amino acid sequence of the light chain variable region of 1C6 (SEQ ID NO: 7) and 2A5 (SEQ ID NO: 8) with the human germline $V_k L18$ amino acid sequence (SEQ ID NO:43). The JK1 sequence shown is SEQ ID NO: 50.

FIG. 9 shows the results of Biacore and fluorescence spectroscopy experiments demonstrating the loss of SDF-1 dimerization as a function of time after dilution in PBS buffer but not in PBS buffer supplemented with 1 mM $CaCl_2$. (A) Effect of 1 mM $CaCl_2$ on the loss of SDF-1 dimers as a function of time after dilution, based on anisotropy measurements. (B) Effect of 1 mM $CaCl_2$ on the loss of SDF-1 dimers as a function of time after dilution, based on FRET measurements.

FIG. 13-2 shows the results of in vivo treatment with anti-SDF-1 antibodies in collagen-induced arthritis. (C) mean score on day 15, (D) mean paw (thickness) on day 15.

FIG. 13-3 shows the results of in vivo treatment with anti-SDF-1 antibodies in collagen-induced arthritis. (E) mean disease score, (F) mean disease score on day 24.

FIG. 14 shows the results of in vivo air pouch experiments demonstrating that anti-SDF-1 antibodies block the migration of leukocytes into the air pouch. (A) Measure of the total cell number in the air pouch. (B) Measure of neutrophils in the air pouch.

FIG. 15 shows the results of in vivo air pouch experiments at lower administrative doses of anti-SDF-1 antibody, demonstrating that anti-SDF-1 antibodies block the migration of leukocytes into the air pouch. (A) Measure of the total cell number in the air pouch. (B) Measure of neutrophils in the air pouch.

FIG. 16 shows the results of an FMAT study demonstrating binding of anti-SDF-1 antibodies on HuVEC cells. (A) rh SDF-1α FMAT analysis with 1C6 antibody. (B) rh SDF-1α FMAT analysis with 2A5 antibody. (C) rh SDF-1α FMAT analysis with I-CAM antibody. (D) rh SDF-1α FMAT analysis with 1D3 and Neg control.

DETAILED DESCRIPTION OF THE INVENTION

Figure 10:
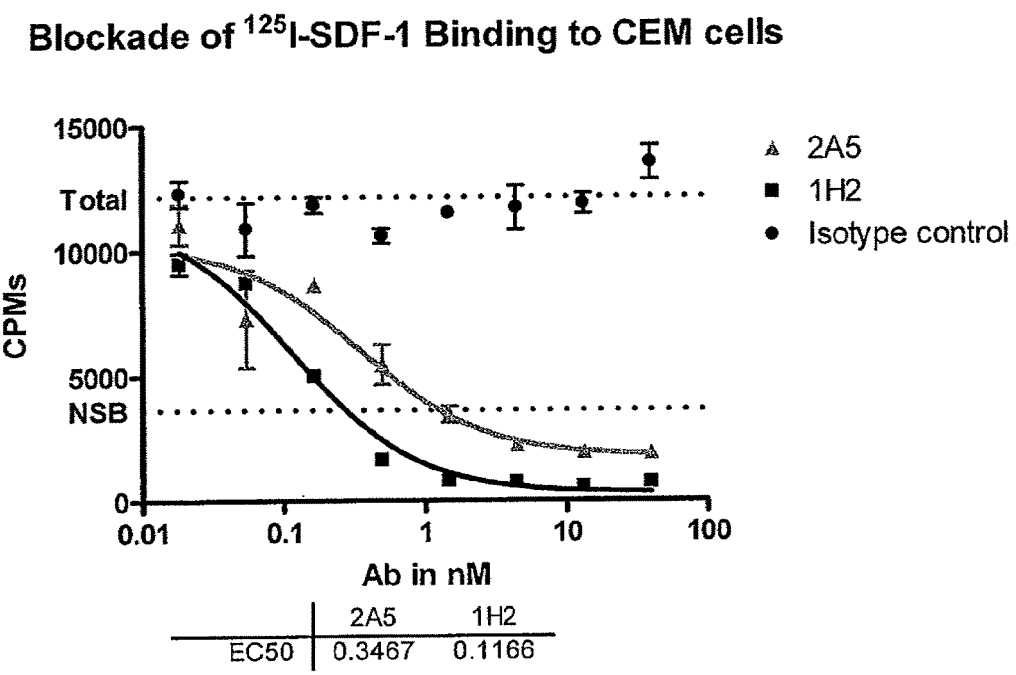
FIG. 10 shows the results of experiments demonstrating that human monoclonal antibodies against SDF-1 block SDF-1 binding to CEM cells.

The present invention relates to isolated monoclonal antibodies, particularly human monoclonal antibodies, that bind specifically to SDF-1 with high affinity. In certain embodiments, the antibodies of the invention are derived from particular heavy and light chain germline sequences and/or comprise particular structural features such as CDR regions comprising particular amino acid sequences. The invention provides isolated antibodies, methods of making such antibodies, immunoconjugates and bispecific molecules comprising such antibodies and pharmaceutical compositions containing the antibodies, immunconjugates or bispecific molecules of the invention. The invention also relates to methods of using the antibodies, such as to detect SDF-1, as well as to treat diseases associated with expression of SDF-1, such as malignancies that express CXCR4 and/or SDF-1, including breast cancer, B-cell malignancies, and metastatic tumors. The invention further relates to methods of using the antibodies to treat autoimmune disorders, such as rheumatoid arthritis (RA) and osteoarthritis (OA), or treat transplant rejection. The invention further relates to methods of using the antibodies to treat proliferative diabetic retinopathy.

In order that the present invention may be more readily understood, certain terms are first defined. Additional definitions are set forth throughout the detailed description.

The terms "Stromal cell-Derived Factor-1" and "SDF-1" are used interchangeably, and include variants, isoforms and species homologs of human SDF-1. Accordingly, human antibodies of this disclosure may cross-react to any of the isoforms of SDF-1. Furthermore, human antibodies of this disclosure may, in certain cases, cross-react with SDF-1 from species other than human. In certain embodiments, the antibodies may be completely specific for one or more human SDF-1 and may not exhibit species or other types of non-human cross-reactivity. The complete amino acid sequence of exemplary human SDF-1 alpha, beta and gamma isoforms has Genbank accession numbers NP_954637 (SEQ ID NO:44), NP_000600 (SEQ ID NO:45) and NP_001029058 (SEQ ID NO:46), respectively.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between various of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the SDF-1 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., SDF-1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds SDF-1 is substantially free of antibodies that specifically bind antigens other than SDF-1). An isolated antibody that specifically binds SDF-1 may, however, have cross-reactivity to other antigens, such as SDF-1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human SDF-1" is intended to refer to an antibody that binds to human SDF-1 with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, even more preferably $5 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Various aspects of the invention are described in further detail in the following subsections.

[Anti-SDF-1 Antibodies]

The antibodies of the invention are characterized by particular functional features or properties of the antibodies. For example, the antibodies bind specifically to human SDF-1. Preferably, an antibody of the invention binds to SDF-1 with high affinity, for example with a $K_D$ of $1 \times 10^{-7}$ M or less. The anti-SDF-1 antibodies of the invention preferably exhibit one or more of the following characteristics:

(i) binds to human SDF-1 with a $K_D$ of $1 \times 10^{-7}$ M or less;
(ii) binds to native human SDF-1 by an immunoprecipitation assay;
(iii) blocks the binding of SDF-1 to CEM cells;
(iv) blocks SDF-1 induced calcium flux in CEM cells;
(v) blocks SDF-1 induced migration of CEM cells; or
(vi) blocks capillary tube formation in HuVEC cells.

Preferably, the antibody binds to human SDF-1 with a $K_D$ of $5 \times 10^{-8}$ M or less, binds to human SDF-1 with a $K_D$ of $2 \times 10^{-8}$ M or less, binds to human SDF-1 with a $K_D$ of $5 \times 10^{-9}$ M or less, binds to human SDF-1 with a $K_D$ of $4 \times 10^{-9}$ M or less, binds to human SDF-1 with a $K_D$ of $3 \times 10^{-9}$ M or less, binds to human SDF-1 with a $K_D$ of $2 \times 10^{-9}$ M or less, or binds to human SDF-1 with a $K_D$ of $1 \times 10^{-9}$ M or less.

The antibody preferably binds to an antigenic epitope present in SDF-1, which epitope is not present in other proteins. The antibody typically binds to SDF-1 but does not bind to other proteins, or binds to other proteins with a low affinity, such as with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

Standard assays to evaluate the binding ability of the antibodies toward SDF-1 are known in the art, including for example, ELISAs, Western blots, RIAs, and flow cytometry analysis. Suitable assays are described in detail in the Examples. The binding kinetics (e.g., binding affinity) of the antibodies also can be assessed by standard assays known in the art, such as by Biacore® system analysis.

[Monoclonal Antibodies 1D3, 1H2, 1C6 and 2A5]

Preferred antibodies of the invention are the human monoclonal antibodies 1D3, 1H2, 1C6 and 2A5, isolated and structurally characterized as described in Examples 1 and 2. The $V_H$ amino acid sequences of 1D3, 1H2, 1C6 and 2A5 are shown in SEQ ID NOs:1, 2, 3 and 4, respectively. The $V_L$ amino acid sequences of 1D3, 1H2, 1C6 and 2A5 are shown in SEQ ID NOs:5, 6, 7 and 8, respectively.

Given that each of these antibodies can bind to SDF-1, the $V_H$ and $V_L$ sequences can be "mixed and matched" to create other anti-SDF-1 binding molecules of the invention. SDF-1 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the invention provides an isolated monoclonal antibody, or antigen binding portion thereof comprising:

(a) a heavy chain variable region comprising an amino acid sequence selected from the group consisting of SEQ ID NOs: 1, 2, 3 and 4; and (b) a light chain variable region comprising an amino acid sequence selected from the group consisting of SEQ ID NOs: 5, 6, 7 and 8;

wherein the antibody specifically binds SDF-1, preferably human SDF-1.

In a preferred embodiment, the antibodies of the present invention further have one or more of the following characteristics:

(i) binds to human SDF-1 with a $K_D$ of $1\times10^{-7}$ M or less;
(ii) binds to native human SDF-1 by an immunoprecipitation assay;
(iii) blocks the binding of SDF-1 to CEM cells;
(iv) blocks SDF-1 induced calcium flux in CEM cells;
(v) blocks SDF-1 induced migration of CEM cells; or
(vi) blocks capillary tube formation in HuVEC cells.

Preferred heavy and light chain combinations include:

(a) a heavy chain variable region comprising the amino acid sequence of SEQ ID NO:1; and (b) a light chain variable region comprising the amino acid sequence of SEQ ID NO:5; or (a) a heavy chain variable region comprising the amino acid sequence of SEQ ID NO:2; and (b) a light chain variable region comprising the amino acid sequence of SEQ ID NO:6; or (a) a heavy chain variable region comprising the amino acid sequence of SEQ ID NO:3; and (b) a light chain variable region comprising the amino acid sequence of SEQ ID NO:7; or (a) a heavy chain variable region comprising the amino acid sequence of SEQ ID NO:4; and (b) a light chain variable region comprising the amino acid sequence of SEQ ID NO:8.

In another aspect, the invention provides antibodies that comprise the heavy chain and light chain CDR1s, CDR2s and CDR3s of 1D3, 1H2, 1C6 and 2A5, or combinations thereof. The amino acid sequences of the $V_H$ CDR1s of 1D3, 1H2, 1C6 and 2A5 are shown in SEQ ID NOs:9, 10, 11 and 12. The amino acid sequences of the $V_H$ CDR2s of 1D3, 1H2, 1C6 and 2A5 are shown in SEQ ID NOs:13, 14, 15 and 16. The amino acid sequences of the $V_H$ CDR3s of 1D3, 1H2, 1C6 and 2A5 are shown in SEQ ID NOs:17, 18, 19 and 20. The amino acid sequences of the $V_k$ CDR1s of 1D3, 1H2, 1C6 and 2A5 are shown in SEQ ID NOs:21, 22, 23 and 24. The amino acid sequences of the $V_k$ CDR2s of 1D3, 1H2, 1C6 and 2A5 are shown in SEQ ID NOs:25, 26, 27 and 28. The amino acid sequences of the $V_k$ CDR3s of 1D3, 1H2, 1C6 and 2A5 are shown in SEQ ID NOs:29, 30, 31 and 32. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to SDF-1 and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-SDF-1 binding molecules of the invention. SDF-1 binding of such "mixed and matched" antibodies can be tested using the binding assays described above and in the Examples (e.g., ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 1D3, 1H2, 1C6 and 2A5.

Accordingly, in another aspect, the invention provides an isolated monoclonal antibody, or antigen binding portion thereof comprising:

(a) a heavy chain variable region CDR1 comprising an amino acid sequence selected from the group consisting of SEQ ID NOs:9, 10, 11 and 12;

(b) a heavy chain variable region CDR2 comprising an amino acid sequence selected from the group consisting of SEQ ID NOs:13, 14, 15 and 16;

(c) a heavy chain variable region CDR3 comprising an amino acid sequence selected from the group consisting of SEQ ID NOs:17, 18, 19 and 20;

(d) a light chain variable region CDR1 comprising an amino acid sequence selected from the group consisting of SEQ ID NOs:21, 22, 23 and 24;

(e) a light chain variable region CDR2 comprising an amino acid sequence selected from the group consisting of SEQ ID NOs:25, 26, 27 and 28; and (f) a light chain variable region CDR3 comprising an amino acid sequence selected from the group consisting of SEQ ID NOs:29, 30, 31 and 32;

wherein the antibody specifically binds SDF-1, preferably human SDF-1.

In a preferred embodiment, the antibody comprises:

(a) a heavy chain variable region CDR1 comprising SEQ ID NO:9;

(b) a heavy chain variable region CDR2 comprising SEQ ID NO:13;

(c) a heavy chain variable region CDR3 comprising SEQ ID NO:17;

(d) a light chain variable region CDR1 comprising SEQ ID NO:21;

(e) a light chain variable region CDR2 comprising SEQ ID NO:25; and (f) a light chain variable region CDR3 comprising SEQ ID NO:29.

In another preferred embodiment, the antibody comprises:

(a) a heavy chain variable region CDR1 comprising SEQ ID NO:10;

(b) a heavy chain variable region CDR2 comprising SEQ ID NO:14;

(c) a heavy chain variable region CDR3 comprising SEQ ID NO:18;

(d) a light chain variable region CDR1 comprising SEQ ID NO:22;

(e) a light chain variable region CDR2 comprising SEQ ID NO:26; and (f) a light chain variable region CDR3 comprising SEQ ID NO:30.

In another preferred embodiment, the antibody comprises:

(a) a heavy chain variable region CDR1 comprising SEQ ID NO:11;

(b) a heavy chain variable region CDR2 comprising SEQ ID NO:15;

(c) a heavy chain variable region CDR3 comprising SEQ ID NO:19;

(d) a light chain variable region CDR1 comprising SEQ ID NO:23;

(e) a light chain variable region CDR2 comprising SEQ ID NO:27; and (f) a light chain variable region CDR3 comprising SEQ ID NO:31.

In another preferred embodiment, the antibody comprises:

(a) a heavy chain variable region CDR1 comprising SEQ ID NO:12;

(b) a heavy chain variable region CDR2 comprising SEQ ID NO:16;

(c) a heavy chain variable region CDR3 comprising SEQ ID NO:20;

(d) a light chain variable region CDR1 comprising SEQ ID NO:24;

(e) a light chain variable region CDR2 comprising SEQ ID NO:28; and (f) a light chain variable region CDR3 comprising SEQ ID NO:32.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $a_v\beta_3$ antibodies using a heavy and light chain variable CDR3 domain of a murine anti-integrin $a_v\beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 seqeunces of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, the present invention provides monoclonal antibodies comprising one or more heavy and/or light chain CDR3 domains from an antibody derived from a human or non-human animal, wherein the monoclonal antibody is capable of specifically binding to SDF-1. Within certain aspects, the present invention provides monoclonal antibodies comprising one or more heavy and/or light chain CDR3 domain from a non-human antibody, such as a mouse or rat antibody, wherein the monoclonal antibody is capable of specifically binding to SDF-1. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present invention provides monoclonal antibodies comprising one or more heavy and/or light chain CDR3 domain from a human antibody, such as, for example, a human antibody obtained from a non-human animal, wherein the human antibody is capable of specifically binding to SDF-1. Within other aspects, the present invention provides monoclonal antibodies comprising one or more heavy and/or light chain CDR3 domain from a first human antibody, such as, for example, a human antibody obtained from a non-human animal, wherein the first human antibody is capable of specifically binding to SDF-1 and wherein the CDR3 domain from the first human antibody replaces a CDR3 domain in a human antibody that is lacking binding specificity for SDF-1 to generate a second human antibody that is capable of specifically binding to SDF-1. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody. In preferred embodiments, the first human antibody is 1D3, 1H2, 1C6 or 2A5.

[Antibodies Having Particular Germline Sequences]

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a human $V_H$ 1-24 gene, wherein the antibody specifically binds SDF-1. In another preferred embodiment, the invention provides an isolated monoclonal antibody, or an antigen-binding portion thereof, comprising a heavy chain variable region that is the product of or derived from a human $V_H$ 3-7 gene, wherein the antibody specifically binds SDF-1. In yet another preferred embodiment, the invention provides an isolated monoclonal antibody, or an antigen-binding portion thereof, comprising a light chain variable region that is the product of or derived from a human $V_K$ L18 gene, wherein the antibody specifically binds SDF-1. In yet another preferred embodiment, the invention provides an isolated monoclonal antibody, or antigen-binding portion thereof, wherein the antibody:

(a) comprises a heavy chain variable region that is the product of or derived from a human $V_H$ 1-24 or 3-7 gene (which genes encode the amino acid sequences set forth in SEQ ID NOs:41 and 42, respectively);

(b) comprises a light chain variable region that is the product of or derived from a human $V_K$ L18 gene (which genes encode the amino acid sequence set forth in SEQ ID NO:43, respectively); and (c) specifically binds to SDF-1, preferably human SDF-1.

Examples of antibodies having $V_H$ and $V_K$ of $V_H$ 1-24 and $V_K$ L18, respectively, are 1D3 and 1H2. Examples of antibody having $V_H$ and $V_K$ of $V_H$ 3-7 and $V_K$ L18, respectively, are 1C6 and 2A5.

In a preferred embodiment, the antibodies of the present invention further have one or more of the following characteristics:

(i) binds to human SDF-1 with a $K_D$ of $1 \times 10^{-7}$ M or less;
(ii) binds to native human SDF-1 by an immunoprecipitation assay;
(iii) blocks the binding of SDF-1 to CEM cells;
(iv) blocks SDF-1 induced calcium flux in CEM cells;
(v) blocks SDF-1 induced migration of CEM cells; or
(vi) blocks capillary tube formation in HuVEC cells.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

[Homologous Antibodies]

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-SDF-1 antibodies of the invention.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs:1, 2, 3 and 4;

(b) the light chain variable region comprises an amino acid sequence that is at least 80% homologous to an amino acid sequence selected from the group consisting of SEQ ID NOs: 5, 6, 7 and 8; and (c) the antibody binds to human SDF-1 with a $K_D$ of $1 \times 10^{-7}$ M or less; and (d) the antibody binds to native human SDF-1 by an immunoprecipitation assay.

In various embodiments, the antibody can be, for example, a human antibody, a humanized antibody or a chimeric antibody.

In a preferred embodiment, the antibodies of the present invention further have one or more of the following characteristics:

(i) blocks the binding of SDF-1 to CEM cells;
(ii) blocks SDF-1 induced calcium flux in CEM cells;
(iii) blocks SDF-1 induced migration of CEM cells;
(iv) blocks capillary tube formation in HuVEC cells.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs:33, 34, 35, 36, 37, 38, 39 and 40, followed by testing of the encoded altered antibody for retained function (i.e., the functions set forth in (c) and (d) above, as well as the functions set forth in (i)-(iv) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

[Antibodies with Conservative Modifications]

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 1D3, 1H2, 1C6 or 2A5), or conservative modifications thereof, and wherein the antibodies retain the desired functional properties of the anti-SDF-1 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs:17, 18, 19 and 20, and conservative modifications thereof;

(b) the light chain variable region CDR3 sequence comprises an amino acid sequence selected from the group consisting of amino acid sequence of SEQ ID NOs:29, 30, 31 and 32, and conservative modifications thereof; and (c) the antibody binds to human SDF-1 with a $K_D$ of $1 \times 10^{-7}$ M or less; and (d) the antibody binds to native human SDF-1 by an immunoprecipitation assay.

In a preferred embodiment, the antibodies of the present invention further have one or more of the following characteristics:

(i) blocks the binding of SDF-1 to CEM cells;
(ii) blocks SDF-1 induced calcium flux in CEM cells;
(iii) blocks SDF-1 induced migration of CEM cells;
(iv) blocks capillary tube formation in HuVEC cells.

In a preferred embodiment, the heavy chain variable region CDR2 sequence comprises an amino acid sequence selected from the group consisting of amino acid sequences of SEQ ID NOs:13, 14, 15 and 16, and conservative modifications thereof; and the light chain variable region CDR2 sequence comprises an amino acid sequence selected from the group consisting of amino acid sequences of SEQ ID NOs:25, 26, 27 and 28, and conservative modifications thereof. In another preferred embodiment, the heavy chain variable region CDR1 sequence comprises an amino acid sequence selected from the group consisting of amino acid sequences of SEQ ID NOs:9, 10, 11 and 12, and conservative modifications thereof; and the light chain variable region CDR1 sequence comprises an amino acid sequence selected from the group consisting of amino acid sequences of SEQ ID NOs:21, 22, 23 and 24, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) and (d) above, as well as the functions set forth in (i)-(iv) above) using the functional assays described herein.

The heavy chain CDR1 sequence of SEQ ID NO:9, 10, 11 or 12 may comprise one or more conservative sequence modification, such as one, two, three, four, five or more amino acid substitutions, additions or deletions; the light chain CDR1 sequence of SEQ ID NO:21, 22, 23 or 24 may comprise one or more conservative sequence modification, such as one, two, three, four, five or more amino acid substitutions, additions or deletions; the heavy chain CDR2 sequence shown in SEQ ID NO:13, 14, 15 or 16 may comprise one or more conservative sequence modification, such as one, two, three, four, five or more amino acid substitutions, additions or deletions; the light chain CDR2 sequence shown in SEQ ID NO:25, 26, 27 or 28 may comprise one or more conservative sequence modification, such as one, two, three, four, five or more amino acid substitutions, additions or deletions; the heavy chain CDR3 sequence shown in SEQ ID NO:17, 18, 19 or 20 may comprise one or more conservative sequence modification, such as one, two, three, four, five or more amino acid substitutions, additions or deletions; and/or the light chain CDR3 sequence shown in SEQ ID NO:29, 30, 31 or 32 may comprise one or more conservative sequence modification, such as one, two, three, four, five or more amino acid substitutions, additions or deletions.

[Antibodies that Bind to the Same Epitope as Anti-SDF-1 Antibodies of the Invention]

In another embodiment, the invention provides antibodies that bind to the same epitope on human SDF-1 as any of the SDF-1 monoclonal antibodies of the invention (i.e., antibodies that have the ability to cross-compete for binding to SDF-1 with any of the monoclonal antibodies of the invention). In preferred embodiments, the reference antibody for cross-competition studies can be the monoclonal antibody 1D3 (having $V_H$ and $V_L$ sequences as shown in SEQ ID NOs:1 and 5, respectively), or the monoclonal antibody 1H2 (having $V_H$ and $V_L$ sequences as shown in SEQ ID NOs:2 and 6, respectively), or the monoclonal antibody 1C6 (having $V_H$ and $V_L$ sequences as shown in SEQ ID NOs:3 and 7, respectively), or the monoclonal antibody 2A5 (having $V_H$ and $V_L$ sequences as shown in SEQ ID NOs:4 and 8, respectively). Such cross-competing antibodies can be identified based on their ability to cross-compete with 1D3, 1H2, 1C6 or 2A5 in standard SDF-1 binding assays. For example, BIAcore® analysis, ELISA assays or flow cytometry may be used to demonstrate cross-competition with the antibodies of the current invention. The ability of a test antibody to inhibit the binding of, for example, 1D3, 1H2, 1C6 or 2A5, to human SDF-1 demonstrates that the test antibody can compete with 1D3, 1H2, 1C6 or 2A5 for binding to human SDF-1 and thus binds to the same epitope on human SDF-1 as 1D3, 1H2, 1C6 or 2A5. In a preferred embodiment, the antibody that binds to the same epitope on human SDF-1 as 1D3, 1H2, 1C6 or 2A5 is a human monoclonal antibody. Such human monoclonal antibodies can be prepared and isolated as described in the Examples.

[Engineered and Modified Antibodies]

An antibody of the invention further can be prepared using an antibody having one or more of the $V_H$ and/or $V_L$ sequences disclosed herein can be used as starting material to engineer a modified antibody, which modified antibody may have altered properties as compared to the starting antibody. An antibody can be engineered by modifying one or more amino acids within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs:9, 10, 11 and 12, SEQ ID NOs:13, 14, 15 and 16, and SEQ ID NOs:17, 18, 19 and 20, respectively, and a light chain variable region comprising CDR1, CDR2, and CDR3 sequences comprising an amino acid sequence selected from the group consisting of SEQ ID NOs:21, 22, 23 and 24, SEQ ID NOs:25, 26, 27 and 28, and SEQ ID NOs:29, 30, 31 and 32, respectively. Thus, such antibodies contain the $V_H$ and $V_L$ CDR sequences of monoclonal antibodies 1D3, 1H2, 1C6 or 2A5 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and 3-23 (AJ406678).

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (http://vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the invention are those that are structurally similar to the framework sequences used by selected antibodies of the invention, e.g., similar to the $V_H$1-24 framework sequences (SEQ ID NO:41) and/or the $V_H$ 3-7 framework sequences (SEQ ID NO:42) and/or the $V_K$ L18 framework sequences (SEQ ID NO:43) used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the instant disclosure provides isolated anti-SDF-1 monoclonal antibodies, or antigen binding portions thereof, comprising a heavy chain variable region comprising: (a) a $V_H$ CDR1 region comprising an amino acid sequence selected from the group consisting of SEQ ID NOs:9, 10, 11 and 12, or an amino acid sequence having one, two, three, four or five amino acid substitutions, deletions or additions as compared to SEQ ID NOs:9, 10, 11 and 12; (b) a $V_H$ CDR2 region comprising an amino acid sequence selected from the group consisting of SEQ ID NOs:13, 14, 15 and 16, or an amino acid sequence having one, two, three, four or five amino acid substitutions, deletions or additions as compared to SEQ ID NOs:13, 14, 15 and 16; (c) a $V_H$ CDR3 region comprising an amino acid sequence selected from the group consisting of SEQ ID NOs: 17, 18, 19 and 20, or an amino acid sequence having one, two, three, four or five amino acid substitutions, deletions or additions as compared to SEQ ID NOs:17, 18, 19 and 20; (d) a $V_K$ CDR1 region comprising an amino acid sequence selected from the group consisting of SEQ ID NOs:21, 22, 23 and 24, or an amino acid sequence having one, two, three, four or five amino acid substitutions, deletions or additions as compared to SEQ ID NOs:21, 22, 23 and 24; (e) a $V_K$ CDR2 region comprising an amino acid sequence selected from the group consisting of SEQ ID NOs:25, 26, 27 and 28, or an amino acid sequence having one, two, three, four or five amino acid substitutions, deletions or additions as compared to SEQ ID NOs:25, 26, 27 and 28; and (f) a $V_K$ CDR3 region comprising an amino acid sequence selected from the group consisting of SEQ ID NOs:29, 30, 31 and 32, or an amino acid sequence having one, two, three, four or five amino acid substitutions, deletions or additions as compared to SEQ ID NOs:29, 30, 31 and 32.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

As yet another example, for 2A5, amino acid residue #1 (within FR1) of $V_H$ is a glutamine (SEQ ID NO:4) whereas this residue in the corresponding $V_H$3-7 germline sequence is a glutamic acid (SEQ ID NO:42). To return the framework region sequences to their germline configuration, for example, residue #1 within FR1 of the $V_H$ of 2A5 can be "backmutated" from glutamine to glutamic acid. Such "backmutated" antibodies are also intended to be encompassed by the invention.

As yet another example, for 2A5, amino acid residue #6 (within FR1) of $V_H$ is a glutamine (SEQ ID NO:4) whereas this residue in the corresponding $V_H$3-7 germline sequence is a glutamic acid (SEQ ID NO:42). To return the framework region sequences to their germline configuration, for example, residue #6 within FR1 of the $V_H$ of 2A5 can be "backmutated" from glutamine to glutamic acid. Such "backmutated" antibodies are also intended to be encompassed by the invention.

For example, Table 1 below shows a number of amino acid changes in the framework regions of the anti-SDF-1 antibodies 1D3, 1H2, 1C6 and 2A5 that differ from the heavy chain parent germline sequence. To return one or more of the amino acid residues in the framework region sequences to their germline configuration, the somatic mutations can be "backmutated" to the germline sequence by, for example, site-directed mutagenesis or PCR-mediated mutagenesis.

As another example, Table 2 below shows a number of amino acid changes in the framework regions of the anti-SDF-1 antibodies 1D3, 1H2, 1C6 and 2A5 that differ from the light chain parent germline sequence. To return one or more of the amino acid residues in the framework region sequences to their germline configuration, the somatic mutations can be "backmutated" to the germline sequence by, for example, site-directed mutagenesis or PCR-mediated mutagenesis.

The alignment of $V_H$ regions for 1D3 and 1H2, against the parent germline $V_H$1-24 (SEQ ID NO:41) sequence is shown in FIG. 6. The alignment of $V_H$ regions for 1C6 and 2A5 against the parent germline $V_H$3-7 sequence (SEQ ID NO:42)

is shown in FIG. 7. The alignment of $V_K$ regions for 1D3 and 1H2, against the parent germline $V_K$ L18 (SEQ ID NO:43) sequence is shown in FIG. 7. The alignment of $V_K$ regions for 1C6 and 2A5 against the parent germline $V_K$ L18 sequence (SEQ ID NO:43) is shown in FIG. 8.

TABLE 1

Modifications to antibodies 1D3, 1H2, 1C6 and 2A5 from the heavy chain germline configuration.

| Anti-SDF-1 Ab | Amino acid position | Amino acid of antibody | Original amino acid of germline configuration |
|---|---|---|---|
| 1D3 | 1 | E | Q |
|  | 84 | T | S |
| 1H2 | 29 | F | L |
|  | 117 | M | T |
| 1C6 | 9 | R | G |
| 2A5 | 1 | Q | E |
|  | 6 | Q | E |

TABLE 2

Modifications to antibodies 1D3, 1H2, 1C6 and 2A5 from the light chain germline configuration.

| Anti-SDF-1 Ab | Amino acid position | Amino acid of antibody | Original amino acid of germline configuration |
|---|---|---|---|
| 1D3 | 1 | E | A |
|  | 3 | V | Q |
| 1H2 | 1 | E | A |
|  | 3 | V | Q |
| 1C6 | 3 | R | Q |
|  | 4 | M | L |
|  | 11 | V | L |
|  | 39 | T | K |
| 2A5 | 1 | D | A |
|  | 4 | M | L |
|  | 5 | I | T |

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2—CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/$K_{224}$A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)—N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

[Antibody Physical Properties]

The antibodies of the present invention may be further characterized by the various physical properties of the anti-SDF-1 antibodies. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala F A and Morrison S L (2004) *J Immunol* 172:5489-94; Wallick et al (1988) *J Exp Med* 168:1099-109; Spiro R G (2002) *Glycobiology* 12:43 R-56R; Parekh et al (1985) *Nature* 316:452-7; Mimura et al. (2000) *Mol Immunol* 37:697-706). Glycosylation has been known to occur at motifs containing an N—X—S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-SDF-1 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-SDF-1 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning M C (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-SDF-1 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

[Methods of Engineering Antibodies]

As discussed above, the anti-SDF-1 antibodies having $V_H$ and $V_K$ sequences disclosed herein can be used to create new anti-SDF-1 antibodies by modifying the $V_H$ and/or $V_K$ sequences, or the constant region(s) attached thereto. Thus, in another aspect of the invention, the structural features of an anti-SDF-1 antibody of the invention, e.g. 1D3, 1H2, 1C6 or 2A5, are used to create structurally related anti-SDF-1 antibodies that retain at least one functional property of the antibodies of the invention, such as binding to human SDF-1. For example, one or more CDR regions of 1D3, 1H2, 1C6 or 2A5, or mutations thereof, can be combined recombinantly with known framework regions and/or other CDRs to create additional, recombinantly-engineered, anti-SDF-1 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-SDF-1 antibody comprising:

(a) providing: (i) a heavy chain variable region antibody sequence comprising a CDR1 sequence selected from the group consisting of SEQ ID NOs:9, 10, 11 and 12, a CDR2 sequence selected from the group consisting of SEQ ID NOs: 13, 14, 15 and 16, and/or a CDR3 sequence selected from the group consisting of SEQ ID NOs:17, 18, 19 and 20; and/or (ii) a light chain variable region antibody sequence comprising a CDR1 sequence selected from the group consisting of SEQ ID NOs:21, 22, 23 and 24, a CDR2 sequence selected from the group consisting of SEQ ID NOs:25, 26, 27 and 28, and/or a CDR3 sequence selected from the group consisting of SEQ ID NOs:29, 30, 31 and 32;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-SDF-1 antibodies described herein, which functional properties include, but are not limited to:

(a) binds to human SDF-1 with a $K_D$ of $1 \times 10^{-7}$ M or less;

(b) binds to native human SDF-1 by an immunoprecipitation assay;

(c) blocks the binding of SDF-1 to CEM cells;

(d) blocks SDF-1 induced calcium flux in CEM cells;

(e) blocks SDF-1 induced migration of CEM cells; or (f) blocks capillary tube formation in HuVEC cells.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-SDF-1 antibody coding sequence and the resulting modified anti-SDF-1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

[Nucleic Acid Molecules Encoding Antibodies of the Invention]

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the $V_H$ and $V_L$ sequences of the 1D3, 1H2, 1C6 or 2A5 monoclonal antibodies. DNA sequences encoding the $V_H$ sequences of 1D3, 1H2, 1C6 and 2A5 are shown in SEQ ID NOs:33, 34, 35 and 36, respectively. DNA sequences encoding the $V_L$ sequences of 1D3, 1H2, 1C6 and 2A5 are shown in SEQ ID NOs:37, 38, 39 and 40, respectively.

Other preferred nucleic acids of the invention are nucleic acids having at least 80% sequence identity, such as at least 85%, at least 90%, at least 95%, at least 98% or at least 99% sequence identity, with one of the sequences shown in SEQ ID NOs:33, 34, 35, 36, 37, 38, 39 or 40, which nucleic acids encode an antibody of the invention, or an antigen-binding portion thereof.

The percent identity between two nucleic acid sequences is the number of positions in the sequence in which the nucleotide is identical, taking into account the number of gaps and the length of each gap, which need to be introduced for optimal alignment of the two sequences. The comparison of sequences and determination of percent identity between two sequences can be accomplished using a mathematical algorithm, such as the algorithm of Meyers and Miller or the XBLAST program of Altschul described above.

Still further, preferred nucleic acids of the invention comprise one or more CDR-encoding portion of the nucleic acid sequences shown in SEQ ID NOs:33, 34, 35, 36, 37, 38, 39 and 40. In this embodiment, the nucleic acid may encode the heavy chain CDR1, CDR2 and/or CDR3 sequence of 1D3, 1H2, 1C6 or 2A5 or the light chain CDR1, CDR2 and/or CDR3 sequence of 1D3, 1H2, 1C6 or 2A5.

Nucleic acids which have at least 80%, such as at least 85%, at least 90%, at least 95%, at least 98% or at least 99% sequence identity, with such a CDR-encoding portion of SEQ ID NOs:33, 34, 35, 36, 37, 38, 39 or 40 are also preferred nucleic acids of the invention. Such nucleic acids may differ from the corresponding portion of SEQ ID NOs:33, 34, 35, 36, 37, 38, 39 or 40 in a non-CDR coding region and/or in a CDR-coding region. Where the difference is in a CDR-coding region, the nucleic acid CDR region encoded by the nucleic acid typically comprises one or more conservative sequence modification as defined herein compared to the corresponding CDR sequence of 1D3, 1H2, 1C6 or 2A5.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$ (SEQ ID NO: 51), such that the $V_H$ and $V_L$ sequences can be expressed as a contiguous single-chain protein, with the $V_L$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

[Production of Monoclonal Antibodies]

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against SDF-1 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). Preparation and use of the HuMAb Mouse®, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchromosomes, such as a mouse that carries a human heavy chain transgene and a human light chain transchromosome. This mouse is referred to herein as a "KM Mouse®," are described in detail in PCT Publication WO 02/43478 to Ishida et al.

Still further, alternative transgenic animal systems expressing human immunoglobulin genes are available in the art and can be used to raise anti-SDF-1 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-SDF-1 antibodies of the invention. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-SDF-1 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

[Immunization of Human Ig Mice]

When human Ig mice are used to raise human antibodies of the invention, such mice can be immunized with a purified or enriched preparation of SDF-1 antigen and/or recombinant SDF-1, or cells expressing SDF-1, or an SDF-1 fusion protein, as described by Lonberg, N. et al. (1994) *Nature* 368 (6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of SDF-1 antigen can be used to immunize the human Ig mice intraperitoneally.

Detailed procedures to generate fully human monoclonal antibodies to SDF-1 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-SDF-1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® strain can be used, as described in Example 1.

[Generation of Phage-Display Combinatorial Libraries and Screening]

Initial cDNA libraries of antibody variable regions were constructed with the spleens from either a HuMAb Mouse® or KM Mouse® immunized with SDF-1. The antibody variable regions were then cloned into phage expression vectors. Phage selection was performed using the Omniclonal® phage selection method (Biosite Inc, San Diego, Calif.) with biotinylated SDF-1 to screen for variable region fragments with nanomolar affinity (KM spleen) or subnanomolar affinity (HuMAb spleen). Variable region fragments of interest are recloned into a Fab expression vector and the Fab is retested for binding affinity and functional affinity. The N-terminal portion of the variable region, which was primer encoded, was backmutated to germline sequence for each variable region. Whole antibodies were then generated off the high affinity anti-SDF-1 Fabs using standard molecular biology techniques.

[Generation of Hybridomas Producing Human Monoclonal Antibodies]

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie Md.). Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

[Generation of Transfectomas Producing Monoclonal Antibodies]

Antibodies of the invention also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr⁻ CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

[Characterization of Antibody Binding to Antigen]

Antibodies of the invention can be tested for binding to SDF-1 by, for example, standard ELISA. Briefly, microtiter plates are coated with purified SDF-1 at 0.25 μm/ml in PBS, and then blocked with 5% bovine serum albumin in PBS. Dilutions of antibody (e.g., dilutions of plasma from SDF-1-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with SDF-1 immunogen. Hybridomas that bind with high avidity to SDF-1 are subcloned and further characterized. One clone from each hybridoma, which retains the reactivity of the parent cells (by ELISA), can be chosen for making a 5-10 vial cell bank stored at −140° C., and for antibody purification.

To purify anti-SDF-1 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-SDF-1 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using SDF-1 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-SDF-1 human IgGs can be further tested for reactivity with SDF-1 antigen by Western blotting. Briefly, SDF-1 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

The binding specificity of an antibody of the invention may also be determined by monitoring binding of the antibody to cells expressing SDF-1, for example by flow cytometry. Typically, a cell line, such as a CHO cell line, may be transfected with an expression vector encoding a transmembrane form of SDF-1. The transfected protein may comprise a tag, such as a myc-tag, preferably at the N-terminus, for detection using an antibody to the tag. Binding of an antibody of the invention to SDF-1 may be determined by incubating the transfected cells with the antibody, and detecting bound antibody. Binding of an antibody to the tag on the transfected protein may be used as a positive control.

The specificity of an antibody of the invention for SDF-1 may be further studied by determining whether or not the antibody binds to other proteins using the same methods by which binding to SDF-1 is determined.

[Immunoconjugates]

In another aspect, the present invention features an anti-SDF-1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$_{177}$. Method for preparing radioimmunconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985), and Thorpe et al., *Immunol. Rev.*, 62:119-58 (1982).

[Bispecific Molecules]

In another aspect, the present invention features bispecific molecules comprising an anti-SDF-1 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for SDF-1 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR or FcαR expressing effector cells (e.g., monocytes, macrophages or polymorphonuclear cells (PMNs)), and to target cells expressing SDF-1. These bispecific molecules target SDF-1 expressing cells to effector cell and trigger Fc receptor-mediated effector cell activities, such as phagocytosis of an SDF-1 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-SDF-1 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), Fcγ RII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ $M^{-1}$).

The production and characterization of certain preferred anti-Fcγ monoclonal antibodies are described in PCT Publication WO 88/00052 and in U.S. Pat. No. 4,954,617 to Fanger et al., the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol.* 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (Fcα RI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ $M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-SDF-1 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83, and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulthydryl bonding of the C-terminus hinge regions of the two heavy chains. In a particularly preferred embodiment, the hinge region is modified to contain an odd number of sulthydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of aγcounter or a scintillation counter or by autoradiography.

[Pharmaceutical Compositions]

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-SDF-1 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19).

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-SDF-1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-SDF-1 antibody of the invention preferably results in a decrease in severity of disease symptoms, an increase in frequency and duration of disease symptom-free periods, or a prevention of impairment or disability due to the disease affliction. For example, for the treatment of SDF-1$^+$ tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, bio compatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V.V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

[Uses and Methods]

The antibodies, particularly the human antibodies, antibody compositions and methods of the present invention have numerous in vitro and in vivo diagnostic and therapeutic utilities involving the diagnosis and treatment of SDF-1 mediated disorders. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by SDF-1 activity. The methods are particularly suitable for treating human patients having a disorder associated with aberrant SDF-1 expression. When antibodies to SDF-1 are administered together with another agent, the two can be administered in either order or simultaneously.

Given the specific binding of the antibodies of the invention for SDF-1, the antibodies of the invention can be used to specifically detect SDF-1 expression on the surface of cells and, moreover, can be used to purify SDF-1 via immunoaffinity purification.

Breast cancer metastasis occurs in a distinct pattern involving the regional lymph nodes, bone marrow, lung, and liver. It was found that CXCR4 is highly expressed in primary and metastatic human breast cancer cells but is undetectable in normal mammary tissue (Muller et al. (2001) *Nature* 410:50-6). SDF-1 has also been suggested to play a role in metastasis of non-small cell lung cancer, where the cancer cells undergo chemotaxis in response to SDF-1 (Phillips et al. (2003) *Am J Respir Crit Care Med* 167:1676-86). SDF-1 has been suggested to induce high levels of F-actin polymerization and pseudopod formation in breast cancer cells, lung and liver extracts, leading to directional migration of breast cancer cells in vitro. This migration of breast cells has previously been shown to be blocked by antibodies to CXCR4 or CCL21. SDF-1 has also been shown to have a role in Intrahepatic cholangiocarcinoma (ICC) (Ohira et al. (2006) *Am J Pathol* 168:1155-68). In addition, inhibition of the SDF-1 interaction with CXCR4 has been found to be involved in stem cell mobilization and may be a useful therapy for various other cancers, for example, multiple myeloma and non-Hodgkin's lymphoma (Fricker et al. (2006) published ahead of print; Fruehauf and Seeger (2005) *Future Oncol* 1:375-83).

Preferably, cancers whose growth may be inhibited using the antibodies of the invention include metastatic tumors and cancers typically responsive to immunotherapy. Non-limiting examples of preferred cancers for treatment include breast cancer, multiple myeloma and lymphomas (e.g., Hodgkin's and non-Hodgkin's lymphoma, lymphocytic lymphoma, primary CNS lymphoma, T-cell lymphoma). Examples of other cancers that may be treated using the methods of the invention include melanoma (e.g., metastatic malignant melanoma), renal cancer (e.g., renal cell carcinoma), brain tumors, chronic or acute leukemias including acute myeloid leukemia, chronic myeloid leukemia, acute lymphoblastic leukemia, chronic lymphocytic leukemia, and nasopharangeal carcinomas, prostate cancer, colon cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, Kaposi's sarcoma, epidermoid cancer, squamous cell cancer, environmentally induced cancers including those induced by asbestos, e.g., mesothelioma and combinations of said cancers.

Furthermore, the human antibodies, antibody compositions and methods of the present invention can be used to treat a subject with a tumorigenic disorder, e.g., a disorder characterized by the presence of tumor cells expressing SDF-1 including, for example, breast cancer, multiple myeloma, non-Hodgkin's lymphoma (NHL), renal cell carcinomas (RCC), such as clear cell RCC, glioblastoma, breast cancer, brain tumors, nasopharangeal carcinomas, acute lymphocytic leukemia (ALL), chronic lymphocytic leukemia (CLL), Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas.

Accordingly, in one embodiment, the invention provides a method of inhibiting growth of tumor cells in a subject, comprising administering to the subject a therapeutically effective amount of an anti-SDF-1 antibody or antigen-binding portion thereof. Preferably, the antibody is a human anti-SDF-1 antibody (such as any of the human anti-human SDF-1 antibodies described herein). Additionally or alternatively, the antibody may be a chimeric or humanized anti-SDF-1 antibody.

SDF-1 has also been detected in the hyperplastic lining and into the extracellular matrix and perivascular lining, including blood vessel endothelium, of rheumatoid arthritis (RA) and osteoarthritis synovial (OA) sections (Pablos et al. (2003) *J Immunol* 170:2147-52). Northern blot analysis of OA and RA fibroblast-like synoviocytes detected SDF-1 expression that was not induced by proinflammatory cytokines, angiogenic factors, or hypoxia. Removal of heparan sulfate molecules from endothelial cells eliminated SDF-1 immunostaining of these cells, suggesting that SDF-1 accumulates on the endothelial cell surface. It was suggested that increased production of SDF-1 in RA synovium leads to its accumulation on heparitinase-sensitive factors of endothelial cells, and that SDF-1 participates in the angiogenesis associated with chronic inflammation. SDF-1 has been shown to induce neovascularization of brochial mucosa in asthmatic subjects and that blocking CXCR-4, the receptor for SDF-1 attenuates allergic lung inflammation, allergic airway disease, airway hyperreactivity and hypersensitivity-type pulmonary granuloma formation (Hoshino et al. (2003) *Eur Respir J* 21:804-9; Lukacs et al. (2002) *Am J Pathol* 160:1353-60; Gonzalo et al. (2000) *J Immunol* 165:499-508; Hu et al. (2006) *Am J Pathol* 169:424-32).

As such, the human antibodies, antibody compositions and methods of the present invention can be used to treat a subject with an autoimmune disorder, e.g., a disorder characterized by the presence of SDF-1 including, for example, rheumatoid arthritis (RA), osteoarthritis (OA), experimental autoimmune encephalomyelitis, asthma, allergic inflammation, such as allergic lung inflammation, allergic airway disease, airway hyperreactivity and hypersensitivity-type pulmonary granuloma. Additional autoimmune disorders in which the antibodies of the invention can be used include, but are not limited to systemic lupus erythematosus (SLE), insulin dependent diabetes mellitus (IDDM), inflammatory bowel disease (IBD) (including Crohn's Disease, ulcerative colitis and Celiac disease), multiple sclerosis (MS), psoriasis, autoimmune thyroiditis and glomerulonephritis. In addition, the antibodies of the present invention can be used to treat transplant rejection.

Accordingly, in one embodiment, the invention provides a method of treating a subject with an autoimmune disorder comprising administering to the subject a therapeutically effective amount of an anti-SDF-1 antibody or antigen-binding portion thereof. Preferably, the antibody is a human anti-SDF-1 antibody (such as any of the human anti-human SDF-1 antibodies described herein). Additionally or alternatively, the antibody may be a chimeric or humanized anti-SDF-1 antibody.

In patients with proliferative diabetic retinopathy, it was demonstrated that SDF-1 concentrations were significantly increased in the vitreous and correlated with disease severity (Butler et al. (2005) *J Clin Invest* 115:86-93). Treatment of patients with triamcinolone decreased SDF-1 levels in the vitreous with marked disease improvement, reduction of SDF-1 and vascular endothelial growth factor (VEGF) levels, eliminated diffuse macular edema and caused regression of active neovascularization (Brooks et al. (2004) *Arch Opthalmol* 122:1801-7). In a mouse model of proliferative diabetic retinopathy, levels of SDF-1 matching those in patients induced retinopathy in the mice, and intravitreal injection of blocking antibodies to SDF-1 prevented retinal neovascularization. Both SDF-1 and CXCR-4 expression has been seen in eyes with age related macular degeneration (Bhutto et al. (2006) *Br J Opthalmol* 90:906-10).

Accordingly, in one embodiment, the invention provides a method of treating a subject with proliferative diabetic retinopathy, cystoid macular edema or age related macular degeneration comprising administering to the subject a therapeutically effective amount of an anti-SDF-1 antibody or antigen-binding portion thereof. Preferably, the antibody is a human anti-SDF-1 antibody (such as any of the human anti-human SDF-1 antibodies described herein). Additionally or alternatively, the antibody may be a chimeric or humanized anti-SDF-1 antibody.

Circulating pools of CD45+, collagen I+, CXCR4+ fibrocytes have been shown to traffic to areas of fibrosis, including lung fibrosis. Treatment with anti-SDF-1 antibodies has been shown to inhibit intrapulmonary recruitment of CD45+, collagen I+, CXCR4+ fibrocytes and attenuate lung fibrosis (Phillips et al. (2004) *J Clin Invest* 114:438-46).

Accordingly, in one embodiment, the invention provides a method of treating a subject with fibrosis, such as lung fibrosis, comprising administering to the subject a therapeutically effective amount of an anti-SDF-1 antibody or antigen-binding portion thereof. Preferably, the antibody is a human anti-SDF-1 antibody (such as any of the human anti-human SDF-1 antibodies described herein). Additionally or alternatively, the antibody may be a chimeric or humanized anti-SDF-1 antibody.

SDF-1 binding to CXCR4 has also been shown to play a role in ischemic events, including ischemia-induced angiogenesis and coronary microvessel contraction (Mieno et al. (2006) *Ann Thorac Surg* 82:657-63). Accordingly, in one embodiment, the invention provides a method of treating a subject with ischemia, ischemia-induced angiogenesis or coronary microvessel contraction, comprising administering to the subject a therapeutically effective amount of an anti-SDF-1 antibody or antigen-binding portion thereof. Preferably, the antibody is a human anti-SDF-1 antibody (such as any of the human anti-human SDF-1 antibodies described herein). Additionally or alternatively, the antibody may be a chimeric or humanized anti-SDF-1 antibody.

In one embodiment, the antibodies (e.g., human monoclonal antibodies, multispecific and bispecific molecules and compositions) of the invention can be used to detect levels of SDF-1, or levels of cells which contain SDF-1 on their membrane surface, which levels can then be linked to certain disease symptoms. Alternatively, the antibodies can be used to inhibit or block SDF-1 function which, in turn, can be linked to the prevention or amelioration of certain disease symptoms, thereby implicating SDF-1 as a mediator of the disease. This can be achieved by contacting a sample and a control sample with the anti-SDF-1 antibody under conditions that allow for the formation of a complex between the antibody and SDF-1. Any complexes formed between the antibody and SDF-1 are detected and compared in the sample and the control.

In another embodiment, the antibodies (e.g., human antibodies, multispecific and bispecific molecules and compositions) of the invention can be initially tested for binding activity associated with therapeutic or diagnostic use in vitro.

For example, compositions of the invention can be tested using the flow cytometric assays described in the Examples below.

The antibodies (e.g., human antibodies, multispecific and bispecific molecules, immunoconjugates and compositions) of the invention have additional utility in therapy and diagnosis of SDF-1-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing SDF-1; to mediate phagocytosis or ADCC of a cell expressing SDF-1 in the presence of human effector cells, or to block SDF-1 ligand binding to SDF-1.

In a particular embodiment, the antibodies (e.g., human antibodies, multispecific and bispecific molecules and compositions) are used in vivo to treat, prevent or diagnose a variety of SDF-1-related diseases. Examples of SDF-1-related diseases include, among others, breast cancer, rheumatoid arthritis, osteoarthritis, prolific diabetic retinopathy, autoimmune disorders, cancer, non-Hodgkin's lymphoma, acute lymphocytic leukemia (ALL), chronic lymphocytic leukemia (CLL), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma, Multiple Myeloma, Waldenstrom's macroglobulinemia, and other B-cell lymphomas.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-SDF-1 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Co-administration of the human anti-SDF-1 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing SDF-1, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-SDF-1 antibodies linked to anti-Fc-gamma RI or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g., human, humanized, or chimeric antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human, humanized, or chimeric antibodies, multispecific and bispecific molecules and immunoconjugates) of the invention can also be administered together with complement. In certain embodiments, the instant disclosure provides compositions comprising human antibodies, multispecific or bispecific molecules and serum or complement. These compositions can be advantageous when the complement is located in close proximity to the human antibodies, multispecific or bispecific molecules. Alternatively, the human antibodies, multispecific or bispecific molecules of the invention and the complement or serum can be administered separately.

Also within the scope of the present invention are kits comprising the antibody compositions of the invention (e.g., human antibodies, bispecific or multispecific molecules, or immuno conjugates) and instructions for use. The kit can further contain one or more additional reagents, such as an immunosuppressive reagent, a cytotoxic agent or a radiotoxic agent, or one or more additional human antibodies of the invention (e.g., a human antibody having a complementary activity which binds to an epitope in the SDF-1 antigen distinct from the first human antibody).

Accordingly, patients treated with antibody compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of the invention can also be used to target cells expressing FcγR or SDF-1, for example for labeling such cells. For such use, the binding agent can be linked to a molecule that can be detected. Thus, the invention provides methods for localizing ex vivo or in vitro cells expressing Fc receptors, such as FcγR, or SDF-1. The detectable label can be, e.g., a radioisotope, a fluorescent compound, an enzyme, or an enzyme co-factor.

In a particular embodiment, the invention provides methods for detecting the presence of SDF-1 antigen in a sample, or measuring the amount of SDF-1 antigen, comprising contacting the sample, and a control sample, with a human monoclonal antibody, or an antigen binding portion thereof, which specifically binds to SDF-1, under conditions that allow for formation of a complex between the antibody or portion thereof and SDF-1. The formation of a complex is then detected, wherein a difference complex formation between the sample compared to the control sample is indicative the presence of SDF-1 antigen in the sample.

In yet another embodiment, immunoconjugates of the invention can be used to target compounds (e.g., therapeutic agents, labels, cytotoxins, radiotoxins immunosuppressants, etc.) to cells which have SDF-1 cell surface receptors by linking such compounds to the antibody. For example, an anti-SDF-1 antibody can be conjugated to any of the toxin compounds described in U.S. Pat. Nos. 6,281,354 and 6,548,530, US patent publication Nos. 20030050331, 20030064984, 20030073852, and 20040087497, or published in WO 03/022806. Thus, the invention also provides methods for localizing ex vivo or in vivo cells expressing SDF-1 (e.g., with a detectable label, such as a radioisotope, a fluorescent compound, an enzyme, or an enzyme co-factor). Alternatively, the immunoconjugates can be used to kill cells which have SDF-1 cell surface receptors by targeting cytotoxins or radiotoxins to SDF-1.

The contents of U.S. Patent Application Ser. No. 60/837,004, filed Aug. 11, 2006, are expressly incorporated herein by reference in its entirety.

The present invention is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against SDF-1

Antibodies were produced using Trans-Phage$^{SM}$ technology, which combines the UltiMAb Human Antibody Development System®, which generates fully human antibodies in a stable transgenic mouse system, and the Omniclonal® phage display technology, which generates custom antibody libraries, and allows for selection from a combinatorial library of antibody heavy and light chains.

[Transgenic HuMAb Mouse® and KM Mouse®]

Fully human monoclonal antibodies to SDF-1 were prepared using the HCo7 strain of the transgenic HuMAb Mouse® and the KM strain of transgenic transchromosomic mice, each of which express human antibody genes. In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,545,806; 5,625,825; and 5,545,807. The KM Mouse® strain contains the SC20 transchromosome as described in PCT Publication WO 02/43478.

[HuMab and KM Immunizations]

To generate fully human monoclonal antibodies to SDF-1, mice of the HuMAb Mouse® and KM Mouse® were immunized with purified recombinant SDF-1α (Peptrotech; Rocky Hill, N.J.). The human isoforms SDF-1α, SDF-1β and SDF-1γ may be used interchangeably, since the extracellular domains are identical. General immunization schemes for the HuMAb Mouse® are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen. A purified recombinant preparation (5-50 μg) of SDF-1α was used to immunize each HuMab Mouse® and KM Mouse®.

Transgenic mice were immunized twice with antigen in complete Freund's adjuvant or Ribi adjuvant either intraperitonealy (IP), subcutaneously (Sc) or via footpad (FP), followed by 3-21 days IP, Sc or FP immunization (up to a total of 11 immunizations) with the antigen in incomplete Freund's or Ribi adjuvant. The immune response was monitored by retroorbital bleeds. The serum was screened by ELISA (as described below), and mice with sufficient titers of anti-SDF-1 human immunogolobulin were used for fusions. Mice were boosted intravenously with antigen 3 and 2 days before sacrifice and removal of the spleen.

[Selection of a HuMab Mouse® or KM Mouse® Producing Anti-SDF-1 Antibodies]

To select a HuMab Mouse® or KM Mouse® producing antibodies that bound SDF-1, sera from immunized mice was tested by ELISA as described by Fishwild, D. et al. (1996) (supra). Briefly, microtiter plates were coated with purified recombinant SDF-1 at 1-2 μg/ml in PBS, 50 μl/wells incubated 4° C. overnight then blocked with 200 μl/well of 5% chicken serum in PBS/Tween (0.05%). Dilutions of plasma from SDF-1-immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-SDF-1 antibodies were used for antibody generation.

[Generation of Phage-Display Combinatorial Libraries and Screening]

Initial cDNA libraries of antibody variable regions were constructed with the spleens from either a HuMAb Mouse® or KM Mouse® immunized with SDF-1. The antibody variable regions were then cloned into phage expression vectors. Phage selection was performed using the Omniclonal® phage selection method (Biosite Inc, San Diego, Calif.) with biotinylated SDF-1 to screen for variable region fragments with nanomolar affinity (KM spleen) or subnanomolar affinity (HuMAb spleen). Variable region fragments of interest are recloned into a Fab expression vector and the Fab is retested for binding affinity and functional affinity. The N-terminal portion of the variable region, which was primer encoded, was backmutated to germline sequence for each variable region. Whole antibodies were then generated off the high affinity anti-SDF-1 Fabs using standard molecular biology techniques.

[Generation of Hybridomas Producing Human Monoclonal Antibodies to SDF-1]

As an alternative method, the mouse splenocytes, isolated from a HuMab Mouse® and/or a KM Mouse®, are fused with PEG to a mouse myeloma cell line either using PEG based upon standard protocols or electric field based electrofusion using a Cyto Pulse large chamber cell fusion electroporator (Cyto Pulse Sciences, Inc., Glen Burnie, Md.). The resulting hybridomas are then screened for the production of antigen-specific antibodies. Single cell suspensions of splenic lymphocytes from immunized mice are fused to one-fourth the number of SP2/0 nonsecreting mouse myeloma cells (ATCC, CRL 1581) with 50% PEG (Sigma). Cells are plated at approximately $1\times10^5$/well in flat bottom microtiter plate, followed by about a two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells are cultured in medium in which the HAT is replaced with HT. Individual wells are then screened by ELISA (described above) for human anti-SDF-1 monoclonal IgG antibodies. Once extensive hybridoma growth occurs, medium is monitored usually after 10-14 days. The antibody secreting hybridomas are replated, screened again and, if still positive for human IgG, anti-SDF-1 monoclonal antibodies are subcloned at least twice by limiting dilution. The stable subclones are then cultured in vitro to generate small amounts of antibody in tissue culture medium for further characterization.

Hybridoma clones 1D3 and 1H2, generated from a KM Mouse®, and 1C6 and 2A5, generated from a HuMAb Mouse®, were selected for further analysis.

Example 2

Structural Characterization of Human Monoclonal Antibodies 1D3, 1H2, 1C6 and 2A5

The cDNA sequences encoding the heavy and light chain variable regions of the 1D3, 1H2, 1C6 and 2A5 monoclonal antibodies were obtained from the 1D3, 1H2, 1C6 and 2A5 hybridomas, respectively, using standard PCR techniques and were sequenced using standard DNA sequencing techniques.

The nucleotide and amino acid sequences of the heavy chain variable region of 1D3 are shown in FIG. 1A and in SEQ ID NO:33 and 1, respectively.

The nucleotide and amino acid sequences of the light chain variable region of 1D3 are shown in FIG. 1B and in SEQ ID NO:37 and 5, respectively.

Comparison of the 1D3 heavy chain immunoglobulin sequence to the known human germline immunoglobulin heavy chain sequences demonstrated that the 1D3 heavy chain utilizes a $V_H$ segment from human germline $V_H$1-24, a D segment from the human germline 6-19, and a JH segment from human germline JH 6b. The alignment of the 1D3 $V_H$ sequence to the germline $V_H$ 1-24 sequence is shown in FIG. 5. Further analysis of the 1D3 $V_H$ sequence using the Kabat system of CDR region determination led to the delineation of the heavy chain CDR1, CDR2 and CD3 regions as shown in FIGS. 1A and 5, and in SEQ ID NOs:9, 13 and 17, respectively.

Comparison of the 1D3 light chain immunoglobulin sequence to the known human germline immunoglobulin light chain sequences demonstrated that the 1D3 light chain utilizes a $V_L$ segment from human germline $V_K$L18 and a JK segment from human germline JK 4. The alignment of the 1D3 $V_L$ sequence to the germline $V_K$L18 sequence is shown in FIG. 7. Further analysis of the 1D3 $V_L$ sequence using the Kabat system of CDR region determination led to the delineation of the light chain CDR1, CDR2 and CD3 regions as shown in FIGS. 1B and 7, and in SEQ ID NOs:21, 25 and 29, respectively.

The nucleotide and amino acid sequences of the heavy chain variable region of 1H2 are shown in FIG. 2A and in SEQ ID NO:34 and 2, respectively.

The nucleotide and amino acid sequences of the light chain variable region of 1H2 are shown in FIG. 2B and in SEQ ID NO:38 and 6, respectively.

Comparison of the 1H2 heavy chain immunoglobulin sequence to the known human germline immunoglobulin heavy chain sequences demonstrated that the 1H2 heavy chain utilizes a $V_H$ segment from human germline $V_H$ 1-24, a D segment from the human germline 6-19, and a JH segment from human germline JH 6b. The alignment of the 1H2 $V_H$ sequence to the germline $V_H$ 1-24 sequence is shown in FIG. 5. Further analysis of the 1H2 $V_H$ sequence using the Kabat system of CDR region determination led to the delineation of the heavy chain CDR1, CDR2 and CD3 regions as shown in FIGS. 2A and 5, and in SEQ ID NOs:10, 14 and 18, respectively.

Comparison of the 1H2 light chain immunoglobulin sequence to the known human germline immunoglobulin light chain sequences demonstrated that the 1H2 light chain utilizes a $V_L$ segment from human germline $V_K$L18 and a JK segment from human germline JK 4. The alignment of the 1H2 $V_L$ sequence to the germline $V_K$L18 sequence is shown in FIG. 7. Further analysis of the 1H2 $V_L$ sequence using the Kabat system of CDR region determination led to the delineation of the light chain CDR1, CDR2 and CD3 regions as shown in FIGS. 2B and 7, and in SEQ ID NOs:22, 26 and 30, respectively.

The nucleotide and amino acid sequences of the heavy chain variable region of 1C6 are shown in FIG. 3A and in SEQ ID NO:35 and 3, respectively.

The nucleotide and amino acid sequences of the light chain variable region of 1C6 are shown in FIG. 3B and in SEQ ID NO:39 and 7, respectively.

Comparison of the 1C6 heavy chain immunoglobulin sequence to the known human germline immunoglobulin heavy chain sequences demonstrated that the 1C6 heavy chain utilizes a $V_H$ segment from human germline $V_H$ 3-7, a D segment from the human germline 7-27, and a JH segment from human germline JH 6b. The alignment of the 1C6 $V_H$ sequence to the germline $V_H$ 3-7 sequence is shown in FIG. 6. Further analysis of the 1C6 $V_H$ sequence using the Kabat system of CDR region determination led to the delineation of the heavy chain CDR1, CDR2 and CD3 regions as shown in FIGS. 3A and 6, and in SEQ ID NOs:11, 15 and 19, respectively.

Comparison of the 1C6 light chain immunoglobulin sequence to the known human germline immunoglobulin light chain sequences demonstrated that the 1C6 light chain utilizes a $V_L$ segment from human germline $V_K$ L18 and a JK segment from human germline JK 1. The alignment of the 1C6 $V_L$ sequence to the germline $V_K$ L18 sequence is shown in FIG. 8. Further analysis of the 1C6 $V_L$ sequence using the Kabat system of CDR region determination led to the delineation of the light chain CDR1, CDR2 and CD3 regions as shown in FIGS. 3B and 8, and in SEQ ID NOs:23, 27 and 31, respectively.

The nucleotide and amino acid sequences of the heavy chain variable region of 2A5 are shown in FIG. 4A and in SEQ ID NO:36 and 4, respectively.

The nucleotide and amino acid sequences of the light chain variable region of 2A5 are shown in FIG. 4B and in SEQ ID NO:40 and 8, respectively.

Comparison of the 2A5 heavy chain immunoglobulin sequence to the known human germline immunoglobulin heavy chain sequences demonstrated that the 2A5 heavy chain utilizes a $V_H$ segment from human germline $V_H$ 3-7, a D segment from the human germline 7-27, and a JH segment from human germline JH 6b. The alignment of the 2A5 $V_H$ sequence to the germline $V_H$ 3-7 sequence is shown in FIG. 6. Further analysis of the 2A5 $V_H$ sequence using the Kabat system of CDR region determination led to the delineation of the heavy chain CDR1, CDR2 and CD3 regions as shown in FIGS. 4A and 6, and in SEQ ID NOs:12, 16 and 20, respectively.

Comparison of the 2A5 light chain immunoglobulin sequence to the known human germline immunoglobulin light chain sequences demonstrated that the 2A5 light chain utilizes a $V_L$ segment from human germline $V_K$ L18 and a JK segment from human germline JK 1. The alignment of the 2A5 $V_L$ sequence to the germline $V_K$ L18 sequence is shown in FIG. 8. Further analysis of the 2A5 $V_L$ sequence using the Kabat system of CDR region determination led to the delineation of the light chain CDR1, CDR2 and CD3 regions as shown in FIGS. 4B and 8, and in SEQ ID NOs:24, 28 and 32, respectively.

Example 3

Characterization of Binding Specificity and Binding Kinetics of Anti-SDF-1 Human Monoclonal Antibodies In this example, binding affinity and binding kinetics of anti-SDF-1 antibodies were examined by Biacore analysis and Western immunoblot analysis.

[Binding Affinity and Kinetics]

Anti-SDF-1 antibodies were characterized for affinities and binding kinetics by Biacore analysis (Biacore AB, Uppsala, Sweden). Purified anti-SDF-1 monoclonal antibodies were covalently linked to a CM5 chip (carboxy methyl dextran coated chip) via primary amines, using standard amine coupling chemistry and kit provided by Biacore. Binding was measured by flowing the SDF-1 (Peprotech, Rocky Hill, N.J.) in PBS buffer (pH7.4) at concentrations of 40, 30, 20, 10, and 5 nM at a flow rate of 75 µl/min. The SDF-1 was injected immediately after dilution to maximize the dimer population. The antigen-antibody association kinetics was followed for 2 minutes and the dissociation kinetics was followed for 8 minutes. The association and dissociation curves were fit to a 1:1 Langmuir binding model using BIAevaluation software (Biacore AB). The $K_D$, $k_{on}$ and $k_{off}$ values that were determined are shown in Table 3.

TABLE 3

| Biacore binding data for SDF-1 HuMAbs. | | | |
|---|---|---|---|
| Anti-SDF-1 antibody | Affinity $K_D \times 10^{-9}$ (M) | On rate $k_{on} \times 10^5$ (1/Ms) | Off rate $k_{off} \times 10^{-4}$ 1/s |
| 1D3 | 0.63 | 8.0 | 5.0 |
| 1H2 | 1.32 | 6.0 | 8.4 |
| 1C6 | 0.46 | 14 | 6.4 |
| 2A5 | 0.37 | 29 | 11 |

[Immunoprecipitation and Western Blot for SDF-1]

Anti-SDF-1 antibodies were characterized for binding to native SDF-1 by immunoprecipitation and subsequent Western blot analysis.

A preparation of $4.5 \times 10^8$ of platelets was made and one T75 flask each of 90-95% confluent cells of CHO—SDF, CHO—S and MCF7 cells was prepared. The cells were washed twice with cold PBS. The cells were lysed in 1.5 ml of lysis buffer (Roche Immunoprecipitation Kit, Cat#1719394) and disrupted by sonicating on ice using five 1-second bursts. The mixture was centrifuged at 12000×g for 10 minutes and the supernatant was collected. The protein concentration was determined using a Micro BCA Protein Assay kit (PIERCE, Cat#23235). The cell lysates were precleared by adding 50 µl protein G agarose to the mixture and incubated at 2-8° C. for 3 hours. Five µg of the anti-SDF-1 antibody 2A5 or an isotype control antibody was added to 500 µg of platelets and one of the CHO—SDF, CHO—S and MCF7 cell lyses and incubated for 1 hour at 2-8° C. on a rocking platform. The antibody-SDF-1 complex was immunoprecipitated by adding 50 µl protein G agarose to the mixture and incubated overnight at 2-8° C. on a rocking platform. The beads were pelleted by centrifugation at 12,000×g for 1 minute. The beads were then washed 6 times with washer buffers (Roche Immunoprecipitation Kit, Cat#1719394). For Western analysis, 60 µl LDS loading buffer (Invitrogen, Cat#NP0007) was added to each sample and heated to 100° C. for 3 minutes to denature the protein. Standard Western blot techniques were used and blotted with 3 µg/ml 2A5 mouse chimeric antibody for 1 hour at room temperature. The results show that the anti-SDF-1 antibody binds to a band of approximately 8 KDa, corresponding with the molecular weight of SDF-1.

Example 4

Biacore and Fluorescence Spectroscopy Based Methods to Characterize the Oligomeric States of SDF-1

The oligomerization state of SDF-1 was determined by fluorescence anisotropy and fluorescence resonance energy transfer (FRET) experiments. Both sets of experiments were performed on a Spex Fluorolog 3.2 instrument (Spex, Edison, N.J.).

The fluorescence anisotropy experiments utilized fluorescein labeled SDF-1. The experiment was performed with excitation at 494 nm and emission monitored at 514 nm and slits set to a band pass of 5 nm. In these experiments a 12.5 µM solution of SDF-1 was diluted to 50 nM and the anisotropy measured as a function of time. These experiments were performed in PBS, PBS and 1 mM $CaCl_2$. Anisotropy, which is a function of total mass and shape of the molecular complex decreases in the absence of $CaCl_2$, but stays constant with the addition of 1 mM $CaCl_2$.

The FRET experiments used dansyl-labeled SDF-1 and fluorescein-labeled SDF-1. These experiments were performed with 335 nm excitation and 520 nm emission and the band pass on the spectrometer was set to 5 nm. In these experiments a 12.5 µM solution of SDF-1 was diluted to 50 nM and the FRET signal measured as a function of time. These experiments were performed in PBS and PBS+1 mM $CaCl_2$. The results are shown in FIG. 9. FIG. 9A shows the effect of 1 mM $CaCl_2$ on the loss of SDF-1 dimers as a function of time after dilution, based on anisotropy measurements. FIG. 9B shows the effect of 1 mM $CaCl_2$ on the loss of SDF-1 dimers as a function of time after dilution, based on FRET measurements. The fluorescence anisotropy and FRET experiments demonstrate the loss of SDF-1 dimerization as a function of time after dilution in PBS buffer but not in PBS buffer supplemented with 1 mM $CaCl_2$.

Example 5

Thermostability of Anti-Sdf-1 Monoclonal Antibodies by Differential Scanning Calorimetry The thermal stability of the anti-SDF-1 monoclonal antibodies was determined using calorimetric analysis of the melting temperature of the antibody.

Calorimetric measurements of melting temperatures ($T_m$) were carried out on a VP-Capillary DSC differential scanning microcalorimeter platform that is combined with an autosampler (MicroCal LLC, Northampton, Mass., USA). Sample cell volume is 0.144 mL. Denaturation data was obtained by heating the samples, at a concentration of 2.0 µM, from 30 to 95° C. at a rate of 1° C./min. The protein samples were present in phosphate-buffered saline (PBS) at pH 7.4. The same buffer was used in the reference cell to obtain the molar heat capacity by comparison. The observed thermograms were baseline corrected and normalized data analyzed based on a non-2-step model, using the software Origin v7.0. The data is shown in Table 4. The anti-SDF-1 monoclonal antibody 2A5 is more stable by differential scanning calorimetry compared to 1C6, 1H2 and 1D3.

TABLE 4

Differential scanning calorimetry data for SDF-1 HuMAbs.

| Anti-SDF-1 antibody | $T_m1$ (° C.) | $T_m2$ (° C.) |
|---|---|---|
| 1D3 | 57.8 | 65.8 |
| 1H2 | 59.9 | 65.7 |
| 1C6 | 59.6 | 66.8 |
| 2A5 | 68.6 | 75.0 |

Example 6

Methods for Physical Stability Under Chemical Denaturation

The stability of anti-SDF-1 monoclonal antibodies were compared by measuring the midpoint of chemical denaturation by fluorescence spectroscopy.

Fluorescence measurements of chemical denaturation were performed on a SPEX Fluorolog 3.22 equipped with a Micromax plate reader (SPEX, Edison, N.J.). The measurements were performed on antibody samples that had been left for 24 hours to equilibrate in 16 different concentrations of guanidinium hydrochloride in PBS buffer. The measurements were made in black, low volume, non-binding surface 384-well plates (Corning, Acton, Mass.) and required 1 µM of antibody in a well volume of 12 µL. Fluorescence was excited at 280 nm and the emission spectra were measured between 300 and 400 nm. The scan speed was 1 second per nm and slits were set to 5 nm bandpass. A buffer blank was performed using PBS and automatically subtracted from the data. Data was fitted to a two-state denaturation model using the GraphPad Prism software. The data are shown in Table 5.

TABLE 5

The chemical denaturation of anti SDF-1 monoclonal antibodies determined by fluorescence spectroscopy

| Clone | Unfolding Midpoint (M) |
|---|---|
| Z2/A5 | 2.63 |
| B1/H2 | 1.96 |
| Z1/C6 | 1.94 |
| B1/D3 | 1.94 |

Example 7

Methods for Epitope Mapping Based on Native and Synthetic Peptides by Mass Spectrometry and Biacore There are two approaches for the mass spectrometric sequence identification of molecular epitopes on the chemokine: epitope extraction and epitope excision. In epitope extraction, the chemokine is first subjected to enzymatic digestion, then its peptide fragments are mixed with anti-chemokine antibody-bound POROS resin to check for binders; whereas in epitope excision, the digestion is performed in situ while the chemokine is bound to the antibody.

[Method to Study the Synthetic Peptides Binding to Mabs by Mass Spectrometry]

After washing away the non-binders, the epitope containing peptide(s) that was still bound onto the antibody resin was taken together directly for MALDI-MS analysis, or eluted off separately from the antibody and analyzed by ESI-MS.

Several peptide fragment patterns were generated by using various proteases to cover the entire chemokine sequence. With different overlaps, the chemokine peptides in both reduced and native forms were examined for epitope binding. Multiple enzymes, in combination or in series, may be necessary in order to achieve the tightest cut near the epitope region.

The peptides that have been identified by mass spectrometry as binders to the antibody were identified on the three-dimensional structure of the chemokine, determined by x-ray crystallography and which is available in public domain (www.rcsb.org). By this procedure, it was possible to eliminate certain stretches of amino acids identified by mass spectrometry as false positives, for example, if they were too distal to the core epitope to be recognized by the antibody. Based on the epitope thus mapped, amino acid sequences for synthetic peptides were designed. To further identify key residues in the epitope (functional epitope) peptides with alanine substituted on key positions were also designed for synthesis. Antibody binding to these synthetic peptides were tested on Biacore and/or mass spectrometer.

[Method to Study the Synthetic Peptides Binding to Mabs by Biacore]

The antibodies were covalently linked to a Biacore CM5 chip. Peptides were freshly prepared in 20 mM ammonium acetate buffer, pH 7.0, at a concentration of 10 ug/mL. These peptides were flowed over the antibody surfaces at a flow rate of 10 µl/min for 15 minutes.

Binding of peptides to isotype controls were used as blank signals. Based on this approach, peptides, with native antigen sequences as well as with alanine substitutions, which bound to the antibodies were identified.

Two molecular epitopes were identified from two different populations of huMAbs produced by hybridoma, designated mAb Z and mAb B. Each of these two antibody groups has selective binding to either the monomer or dimer SDF-1α. The anti-SDF-1 antibodies 1D3 and 1H2 are mAb B group antibodies. The anti-SDF-1 antibodies 1C6 and 2A5 are mAb Z group antibodies. The mAb Z group recognizes two epitope peptides, one near the N-terminal region amino acid residues 7-19 which is also the known receptor binding site, and the other one on the third beta strand between residues 37-50. The mAb B group blocks the heparin binding site, which has been shown to be the SDF-1α dimer interface. By inference from the BiaCore data, mAb B binds predominately to the dimer interface, between residues 24-30 of the first and the second monomer, where the heparin also binds. One critical residue, Arg8, involved in epitope binding with mAb Z was also identified by this mass spectrometric based assay.

Example 8

Biacore and Fluorescence Based Methods to Monitor the Variation of SDF-1 Oligomeric States and Mab Binding when the Following Conditions are Changed To measure the binding of the anti-SDF-1 monoclonal antibodies to monomeric SDF-1, a Biacore experiment with a low density of SDF-1 covalently attached to a CM5 chip was performed. For 1C6 and 2A5, binding was measured by flowing the SDF-1 (Peprotech, Rocky Hill, N.J.) in PBS buffer (pH7.4) at concentrations of 50, 40, 30, 20, and 10 nM. For 1D3 and 1H2, binding was measured by flowing the SDF-1 (Peprotech, Rocky Hill, N.J.) in PBS buffer (pH7.4) at concentrations of 500, 400, 300, 200, and 100 nM. The data are shown in Table 6. The 1C6 and 2A5 show much higher affinity for binding to the monomeric form of SDF-1.

TABLE 6

Binding of monoclonal antibodies to monomeric SDF-1

| Anti-SDF-1 antibody | Affinity $K_D \times 10^{-9}$ (M) | On rate $k_{on} \times 10^4$ (1/Ms) | Off rate $k_{off} \times 10^{-4}$ 1/s |
|---|---|---|---|
| 1D3 | 151 | 1.1 | 17 |
| 1H2 | 176 | 0.91 | 16 |
| 1C6 | 3.6 | 11 | 4.0 |
| 2A5 | 4.6 | 9.6 | 4.5 |

The effect of SDF-1 dilution on binding to monoclonal antibodies was monitored by capturing the antibodies on an antiCH1 chip then measuring the SDF-1 binding response after 2 mins of association as a function of time after dilution. These experiments were performed on 1D3 and 1C6 monoclonal antibodies in PBS (pH7.4) and the SDF-1 was diluted from 12.5 µM to 100 nM.

To determine the effect of pH, $Ca^{2+}$ ions, and EDTA on the binding of the anti-SDF-1 monoclonal antibodies to SDF-1α Biacore analysis was performed. The anti-SDF-1 monoclonal antibodies were covalently attached to a CM5 chip (Biacore). In each buffer, 100 nM of SDF-1 was flowed across chip and response measured at the end of 2 minute association phase as a function of time after dilution. Buffers used were HBS-EP (Biacore), HBS-P (lacks EDTA), PBS, PBS+1 mM $CaCl_2$, and sodium acetate pH5.5+150 mM NaCl.

The blocking of SDF-1 binding to heparin sulphate was determined by capturing biotinylated heparin sulphate (Sigma) on a Streptavidin chip (Biacore, Uppsala, Sweden) then measuring the SDF-1 binding with and without an excess of monoclonal antibodies (1H2 and 2A5). Experiments were carried out in PBS.

Example 9

Functional Activity Measured by Blockade of $^{125}$I-SDF-1α Binding to Cells

A comparison of anti-SDF-1α antibodies on blocking SDF-1 binding to CEM cells was performed by a standard radio-labeled ligand binding assay. The anti-SDF-1α antibodies were serially diluted 1:3 to yield a range of concentrations from 40 nM to 2 pM. The antibodies were added to CEM cells in the presence of 100 pM $^{125}$I-SDF-1 with a specific activity of 2000 Ci/mmole (from Amersham catalog #IM314-25UCI). An irrelevant antibody with the same isotype was used as a negative control. The total possible bound radio-labeled ligand was determined by allowing the $^{125}$I-SDF-1 to bind to CEM cells in the absence of antibodies. Non-specific binding of the radio-labeled ligand was determined by allowing the $^{125}$I-SDF-1 to bind in the presence of 1 µM unlabeled SDF-1 (from Peprotech cataolog #300-28A). The results are shown in FIG. 10.

Example 10

Anti-SDF-1 Antibodies Block SDF-1-Induced Calcium Flux in CEM Cells

Figure 11:
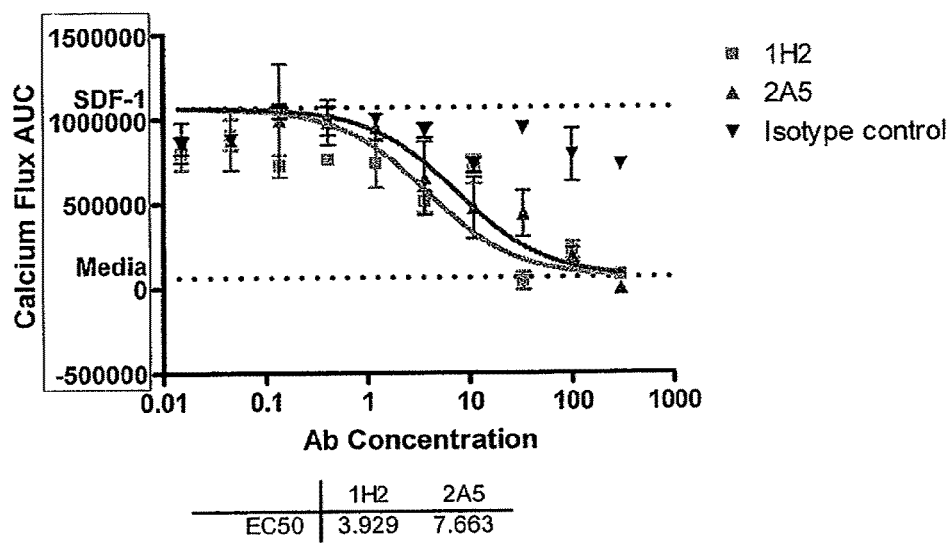
FIG. 11 shows the results of experiments demonstrating that human monoclonal antibodies against SDF-1 block SDF-1 induced calcium flux in CEM cells.

CEM cells were labeled with the fluorescent calcium dye, Calcium 3 (Molecular Devices, Sunnyvale, Calif.). The anti-SDF-1 antibodies were titrated in a 1:3 serial dilution series resulting in a concentration range from 100 nM to 1 pM and mixed with 50 nM SDF-1α (Peprotech, Rocky Hill, N.J.) prior to loading into the Flexstation machine (Molecular Devices). As a negative control, an irrelevant antibody with the same isotype was used. Cells were then stimulated with the SDF-1α/antibody mixtures. Cells without antibody were stimulated with SDF-1α (made up in Hank's buffered saline with 0.1% BSA or HBS) to achieve a maximum possible calcium flux signal. To determine a baseline, cells were stimulated with HBS with 0.1% BSA. The SDF-1α-stimulated release of calcium was measured by a calcium-dependent fluorescence over time. The area under the curve of the resulting fluorescence trace was reported as an indication of calcium flux. The resulting inhibition of calcium flux by the anti-SDF-1 antibodies is represented in FIG. 11. The data was plotted and the EC50s were calculated using GraphPad Prism software and the non-linear curve fit, sigmoidal dose response formula.

Example 11

Anti-SDF-1 Antibodies Block SDF-1-Induced Migration of CEM Cells

Figure 12:
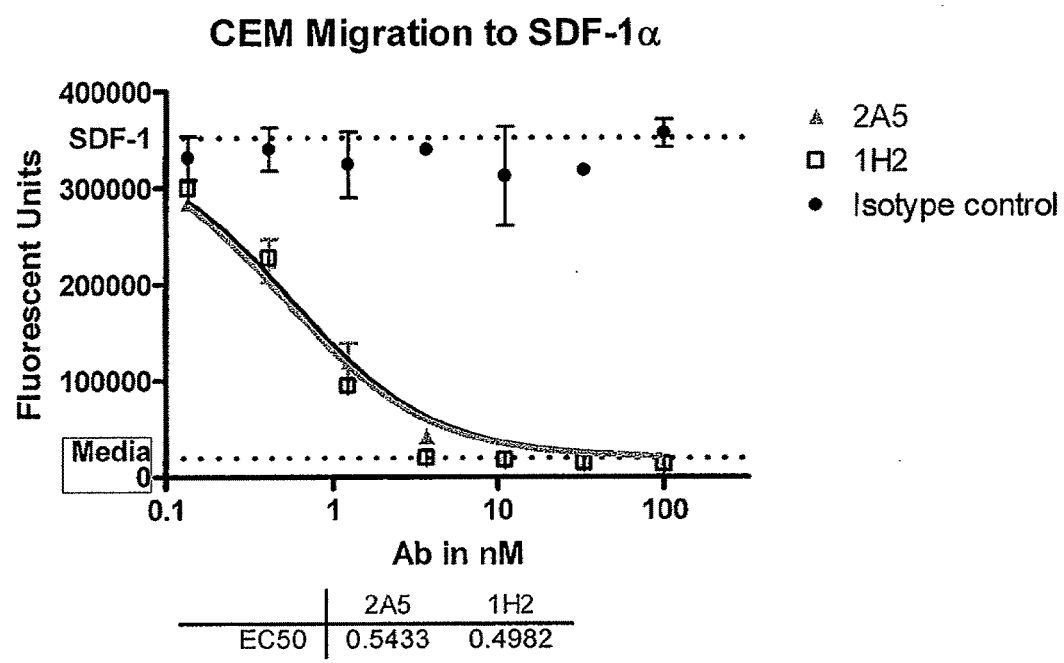
FIG. 12 shows the results of experiments demonstrating that human monoclonal antibodies against SDF-1 block SDF-1 induced migration of CEM cells.

CEM cells were labeled with the BATDA reagent from Perkin Elmer. The anti-SDF-1 antibodies were titrated in a 1:3 serial dilution series resulting in a concentration range from 100 nM to 1 pM and mixed with 5 nM SDF-1α (Peprotech, Rocky Hill, N.J.). As a negative control an irrelevant antibody with the same isotype was used. Recombinant human SDF-1α with or without antibodies was added at 5 nM to the lower chamber of a 96 well Neuroprobe migration plate with 5.7 mm diameter filters per well. Each well contains 5 µm pores. Labeled CEM cells were loaded onto the filters at a concentration of 0.5 million cells per well. The migration plate was incubated at 37° C. for 2.5 hours. Migrated cells are captured in the lower chamber of the plate, lysed and detected with Europium detection solution by Perkin Elmer. The chemi-luminescent signal is recorded on the Fusion instrument. The resulting inhibition of SDF-1α-induced migration by the anti-SDF-1 antibodies are shown in FIG. 12.

Example 12

Treatment of Antibody-Induced Arthritis Using Anti-SDF-1 Antibodies

Collagen-induced arthritis (CIA) in mice is widely used as an experimental screening model for rheumatoid arthritis in humans. In this model mice are immunized with type II collagen that triggers the production of antibodies to particular regions of the type II collagen molecule. The onset of the disease is gradual and 6 weeks is the minimum length in the classical CIA model. More recently, 4 autoantigenic epitopes of the type II collagen were identified and a cocktail of 4 monoclonal antibodies generated against these epitopes was used to induce arthritis. An LPS injection 3 days after the anti-collagen antibody administration induced a rapid manifestation of the disease. In this antibody induced model, the onset of disease is rapid and the whole study can be performed in 2 weeks. This antibody induced model displays features similar to those found in the classical CIA model, such as extensive infiltration of inflammatory cells into the synovium and joining space, pannus formation and marked destruction of bone and cartilage tissues. Hence, this model was used to monitor the efficacy of anti-inflammatory substances in a similar fashion in a much shorter study period than the classical model.

In this experiment, 6-8 week old Balb/c mice were used. On day 0, mice were injected with 4 mg of anti-collagen antibody cocktail (Arthrogen) followed by an injection of 25 µg LPS on day 2. On days 1, 4, 7, and 10 mice were treated with our anti-SDF-1 antibodies, isotype control antibody, PBS, or the corticosteroid, dexamethasone at 15 mg/kg for antibodies and 0.3 mg/kg for dexamethasone. The anti-SDF-1 antibodies tested in this study were clones 1H2, 2A5 and 1C6. Development of arthritis was scored on a scale of 0-4 by clinical observation (redness and swelling) on days 3, 5, 8, 10, 12 and 15. The severity score are 0 for normal, 1 for clear redness or mild swelling of the ankle or wrist, or swelling of one digit, 2 for redness and swelling of the more than one digit, 3 for redness and swelling of the entire paw, metatarsus, hock and/or carpus, 4 for inflamed, swollen or deformed paw, with involvement of multiple joints. Severity scores were assessed for all 4 paws, with a total possible overall score of 16 for each animal. Swelling of all four paws (paw thickness) was measured using a precision caliper on days 3, 5, 8, 10, 12 and 15.

Blood specimens for serum preparation were collected from all mice on two occasions: prior to starting treatment and prior to necropsy. On day 15 animals were sacrificed and two hind paws excised approximately 0.5 cm above the ankle and preserved in 10% neutral buffered formalin for histopathology analysis.

Figure 13:
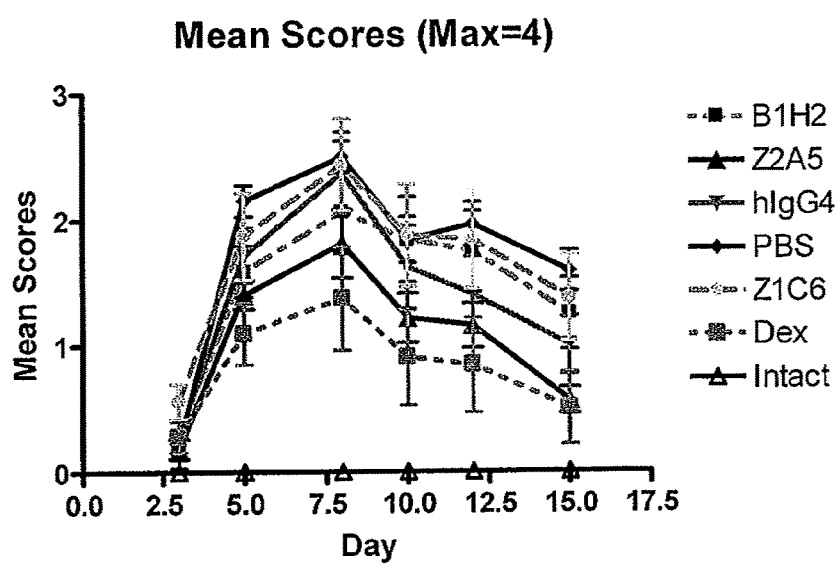
FIG. 13-1 shows the results of in vivo treatment with anti-SDF-1 antibodies in collagen-induced arthritis. (A) mean score, (B) mean paw width.
Figure 1:
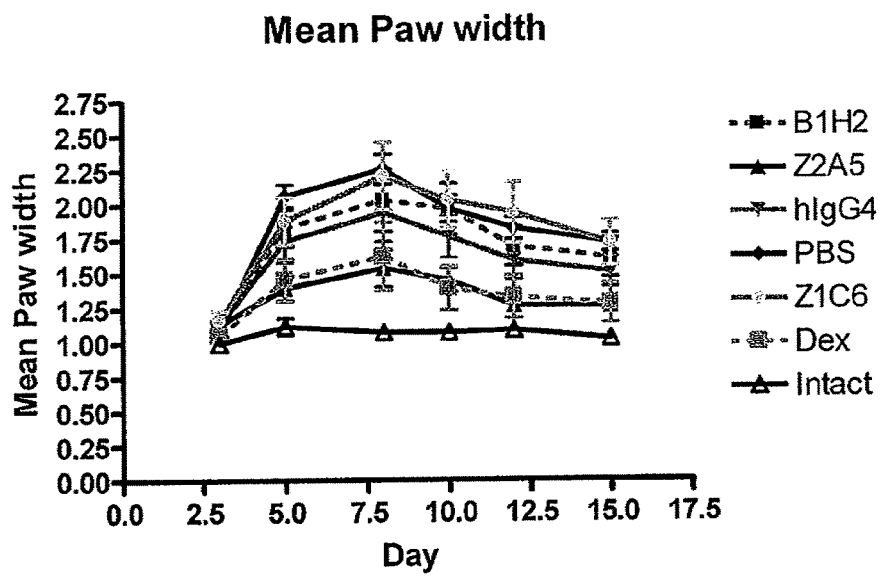
Figure 13:
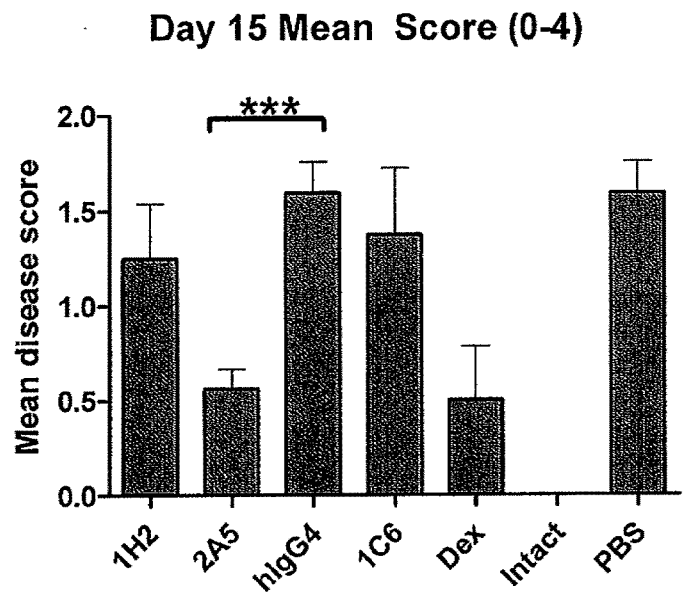
Figure 2:
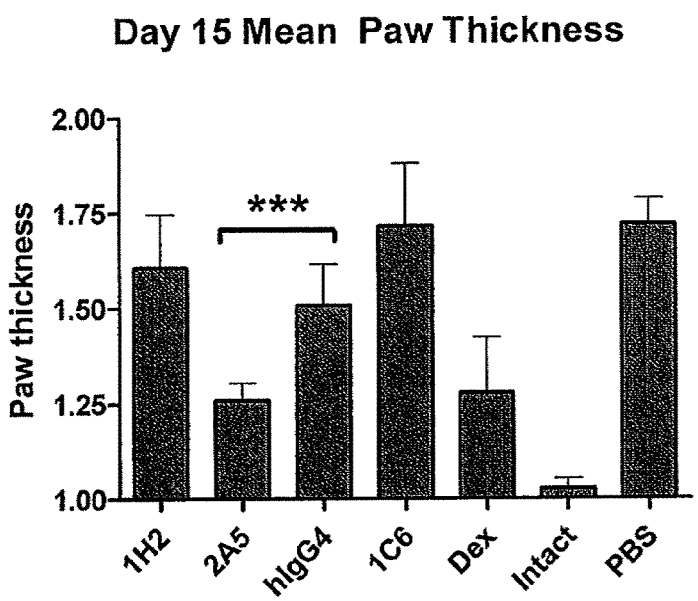
Figure 13:
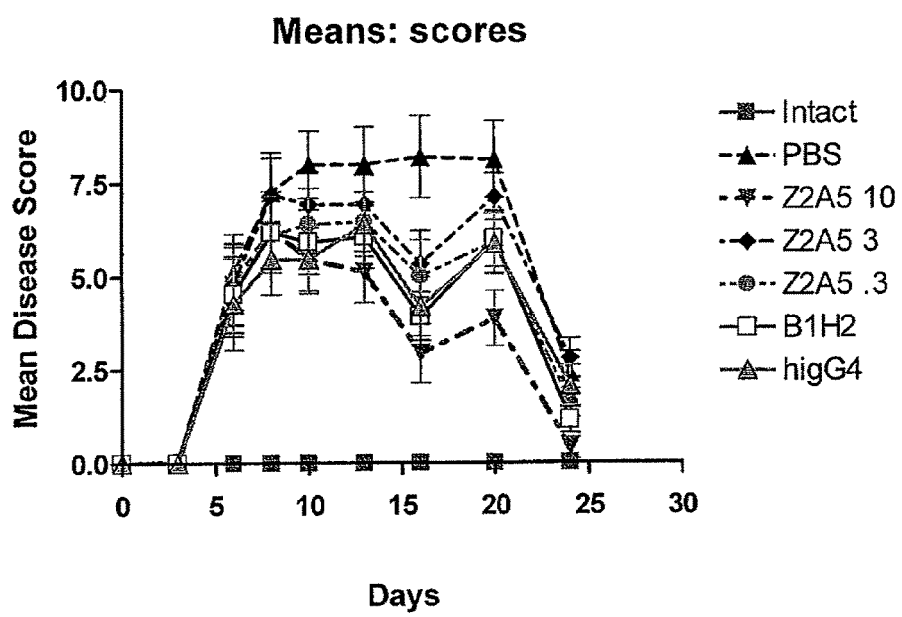
Figure 3:
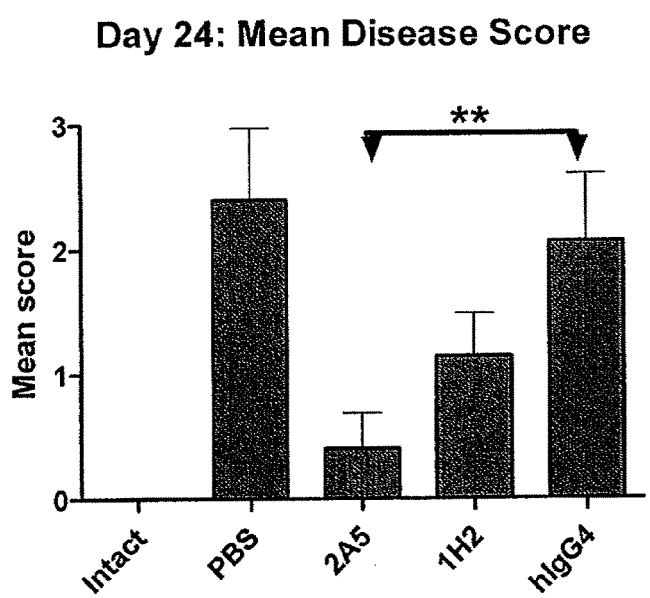

The results are shown in FIGS. 13-1 to 13-3. FIG. 13-1 shows mean score (A) and mean paw width (B) for each mouse. FIG. 13-2 shows mean score (C) and mean paw (thickness) (D) on day 15. FIG. 13-3 shows mean disease score (E) and mean disease score on day 24 (F). Mice treated with 2A5 (black solid upright triangle) developed a significantly less severe disease than mice treated with isotype control (gray Inverted triangle). The disease severity and paw inflammation of the isotype control group was similar to the positive control, dexamethasone (large boxes) The 1H2 group and 1C6 group, however, did not show any benefit with antibody treatment and were comparable to isotype control. A statistical analysis to assess significance of these findings indicated that the effect of the Z2A5 group was significant to a P value of 0.0006 while the effect of the B1H2 group was insignificant (P=0.346.)

Example 13

Efficacy of Anti-SDF-1 Antibodies in the Mouse Air Pouch Model

An air pouch model was developed to test the efficacy of anti-SDF-1 antibodies. In this in vivo model, multiple cell types migrate in response to SDF-1 and the air pouch provides an in vivo microenvironment for cellular migration. Briefly, mice were anesthetized and an air pouch was created by injecting sterile air. On the day of the study, the air pouch was injected with recombinant human SDF-1 alpha in the absence or presence of anti-SDF-1 antibodies. The efficacy of the antibodies was determined. In this example, anti-SDF-1 antibodies 2A5, 1C6, 1D3 and 1H2 were tested.

Female C57BL/6 mice between 8-12 weeks of age (CRL) were anesthetized with isoflorane and an air pouch was created by injecting 5 ml of sterile air subcutaneously in the dorsum of the mice. Three days later, an additional 3 ml of sterile air was injected. On day 7, one ml of PBS, or SDF-1α alone (200 ng, PeproTech) or SDF-1α plus human IgG4 isotype control, or SDF-1α plus 50 µg or 100 µg of anti-SDF-1 antibodies was injected in a 1 ml volume. Five mice were used in each test group. Four hours later, mice were sacrificed by asphyxiation using $CO_2$ and pouches were washed with 2 ml of PBS/5 mM EDTA followed by two additional washes with 3 ml of PBS/5 mM EDTA. The exudates were centrifuged at 500×g for 5 min at room temperature. Cells were counted with a hemacytometer and differential counts of leukocyte subpopulations were performed on cytospin preparation stained with Kwik-Diff staining kit (Thermo Electron Corporation, Waltham, Mass.).

The results are shown in FIG. 14. The results showed that SDF-1α at 400 ng induced migration of leukocytes into the air pouch and the total numbers of leukocytes typically is increased 2-3 fold when compared to PBS-filled air pouches. Anti-SDF-1 antibodies administered at a concentration of 100 μg/ml, completely blocked cell migration back to the level seen with PBS alone (FIG. 14A). Isotype control antibody had no effect. In FIG. 14B we measured the percentage of Neutrophils (Neu) or monocytes/lymphocytes (Others) that migrated. The majority of cells which migrated, represented by the Neutrophils, are blocked with anti-SDF-1 antibodies. Likewise, monocytes and lymphocytes are blocked. At this antibody concentration, no differences were seen in the blocking activity of the tested antibodies.

In the next study the concentration of SDF-1 used to induce migration was reduced to 200 ng and the concentration of antibodies were tested at both 100 μg/ml and a reduced level at 50 μg/ml. Both 2A5 and 1C6 at 50 μg and 100 μg blocked neutrophil, lymphocyte and monocyte migration (FIG. 15). The numbers of neutrophils, lymphocytes and monocytes were completely reduced to PBS levels. The potency was similar between the two antibodies at this concentration. Isotype control at 100 μg had no effect.

In summary, anti-SDF-1 antibodies, 2A5, 1C6, 1H2 and 1D3 are potent inhibitors of in vivo cell migration.

Example 14

Fluorometric Microvolume Assay Technology Fmat Study

In this example, binding of anti-SDF-1 antibodies to SDF-1 in the presence of HuVEC cells was examined. HuVEC cells contain glycosaminoglycans (GAGs) to which SDF-1 binds.

HUVEC (human umbilical vein endothelial cells, Cambrex, P/N CC-2519) cells were plated at 1×10⁴ cells per well in 2004 per well culture medium (Cambrex, P/N CC-3124, with added extra FBS to 10% final) onto 96-well black, clear bottom, opaque plates and incubated at 37° C. with $CO_2$ overnight. Carefully remove cell supernatant. Dilute antigen and antibody at 4× concentration. Add 50 μL assay buffer (PBS plus 0.5% FBS), 50 μL rh SDF-1α (Peprotech, P/N 300-28A), 50 μL antibody, and 50 μL 1:3000 diluted Alexa Fluor 647 goat anti-human IgG (H+L) (Invitrogen, P/N 21445) or goat anti-mouse IgG (H+L) (Invitrogen, P/N 21235). Cover plate with foil and incubate at room temp for 2 hours. Read with Applied Biosystems' FMAT 8200. The results are shown in FIG. 16. This experiment shows that the anti-SDF-1 antibodies 1C6 and 2A5 show better binding to GAG-bound SDF-1 than the anti-SDF-1 antibodies 1D3 and 1H2, suggesting that the antibodies 1D3 and 1H2 bind to an epitope region that overlaps with the GAG binding site.

Example 15

Blockade of $^{125}$I-SDF-1α Binding to GAGs on Non-CXCR4 expressing Cells

In this example, inhibition of SDF-1α binding to non-specific glycosaminoglycans (GAGs) are tested using anti-SDF-1 antibodies.

Figure 17:
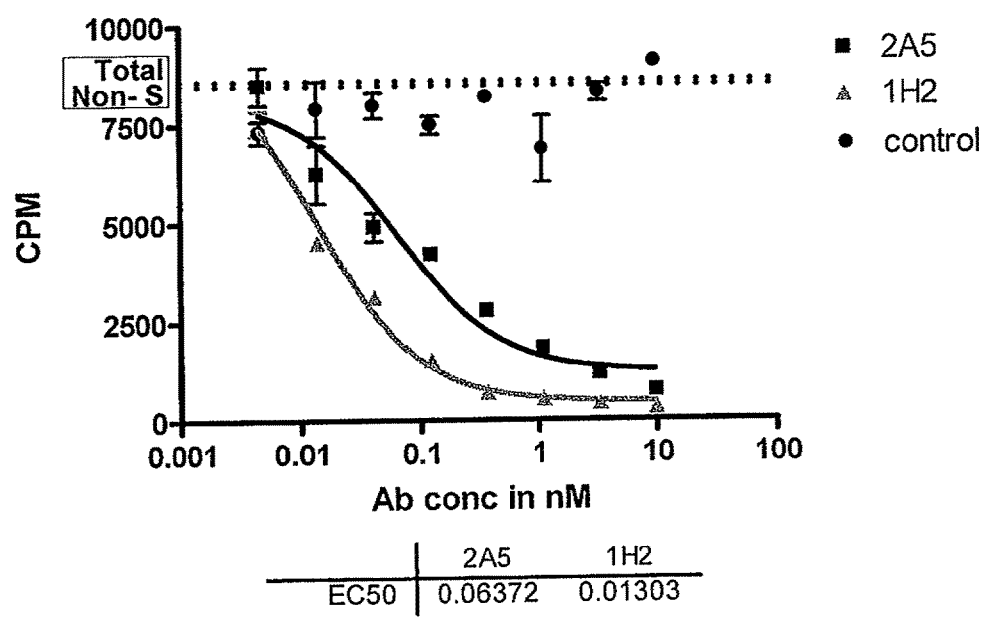
FIG. 17 shows the results of a binding assay showing that antibodies directed against SDF-1 block SDF-1 binding to HuVEC cells.

A comparison of anti-SDF-1 antibodies on blocking SDF-1 binding to HuVEC cells from ATCC (cat# CRL-1730) was performed by a standard radio-labeled ligand binding assay. The anti-SDF-1 antibodies were serially diluted 1:3 to yield a range of concentrations from 10 nM to 0.5 pM. The antibodies were added to HuVEC cells in the presence of 100 pM $^{125}$I-SDF-1α with a specific activity of 2000 Ci/mmole (from Amersham catalog # IM314-25UCI). An irrelevant antibody with the same isotype was used as a negative control. The total possible bound radio-labeled ligand was determined by allowing the $^{125}$I-SDF-1α to bind to HuVEC cells in the absence of antibodies. Non-specific binding of the radio-labeled ligand was determined by allowing the $^{125}$I-SDF-1α to bind in the presence of 1 μM unlabeled recombinant human SDF-1α (from Peprotech cataolog #300-28A). HuVEC cells do not express CXCR4 and thus there is only non-specific binding of SDF-1α to these cells presumably through GAGs. The results are shown in FIG. 17.

Example 16

Anti-SDF-1 Antibodies Block Capillary Tube Formation by HUVEC

In this example, the effect of anti-SDF-1 antibodies on the formation of capillary tube connection points between HuVEC cells was tested.

Matrigel is diluted 1:1 with RPMI and plated onto the wells of a 96 wells plate and allowed to polymerize for 30 minutes at 37° C. HuVEC (from Cambrex cat. #CC-2519) at 80% confluence are trypsanized and resuspended at 1×10⁶ cells per ml in RPMI with 0.5% FBS. Antibodies are well mixed with HuVEC at a final concentration of 3 μg/ml and allowed to incubate at room temperature for 30 minutes. An irrelevant antibody of the same isotype or media was used as a negative control. As a positive control of inhibition of tube formation, a mouse anti-human αVβ3 (CD51/CD61) antibody (from R&D Systems cat #MAB3050) was used. HuVEC with or without antibodies were plated onto the matrigel-coated wells and incubated at 37° C. for 18 hours.

The HuVEC incubated with media or isotype control form capillary tubes resulted in the appearance of connected cells across the plate with 3-5 points of connection or branch points per cell. The HuVEC incubated with either anti-SDF-1 Abs or Anti-αVβ3 antibody did not form capillary tubes. The cells appear isolated and with few or no branch points. The anti-SDF-1 antibody 1H2 yielded very few branch points where as 2A5 produced some branch points in a small percentage of cells.

SUMMARY OF SEQUENCE LISTING

| SEQ ID NO: | SEQUENCE | SEQ ID NO: | SEQUENCE |
|---|---|---|---|
| 1 | VH a.a. 1D3 | 21 | VK CDR1 a.a. 1D3 |
| 2 | VH a.a. 1H2 | 22 | VK CDR1 a.a. 1H2 |
| 3 | VH a.a. 1C6 | 23 | VK CDR1 a.a. 1C6 |
| 4 | VH a.a. 2A5 | 24 | VK CDR1 a.a. 2A5 |

-continued

| SEQ ID NO: | SEQUENCE | SEQ ID NO: | SEQUENCE |
|---|---|---|---|
| 5 | VK a.a. 1D3 | 25 | VK CDR2 a.a. 1D3 |
| 6 | VK a.a. 1H2 | 26 | VK CDR2 a.a. 1H2 |
| 7 | VK a.a. 1C6 | 27 | VK CDR2 a.a. 1C6 |
| 8 | VK a.a. 2A5 | 28 | VK CDR2 a.a. 2A5 |
| 9 | VH CDR1 a.a. 1D3 | 29 | VK CDR3 a.a. 1D3 |
| 10 | VH CDR1 a.a. 1H2 | 30 | VK CDR3 a.a. 1H2 |
| 11 | VH CDR1 a.a. 1C6 | 31 | VK CDR3 a.a. 1C6 |
| 12 | VH CDR1 a.a. 2A5 | 32 | VK CDR3 a.a. 2A5 |
| 13 | VH CDR2 a.a. 1D3 | 33 | VH n.t. 1D3 |
| 14 | VH CDR2 a.a. 1H2 | 34 | VH n.t. 1H2 |
| 15 | VH CDR2 a.a. 1C6 | 35 | VH n.t. 1C6 |
| 16 | VH CDR2 a.a. 2A5 | 36 | VH n.t. 2A5 |
| 17 | VH CDR3 a.a. 1D3 | 37 | VK n.t. 1D3 |
| 18 | VH CDR3 a.a. 1H2 | 38 | VK n.t. 1H2 |
| 19 | VH CDR3 a.a. 1C6 | 39 | VK n.t. 1C6 |
| 20 | VH CDR3 a.a. 2A5 | 40 | VK n.t. 2A5 |
| 41 | VH 1-24 germline a.a. | 42 | VH 3-7 germline a.a. |
| 43 | VK L18 germline a.a. | 44 | SDF-1 alpha a.a. |
| 45 | SDF-1 beta a.a. | 46 | SDF-1 gamma a.a. |
| 47 | JH6b germline a.a. | 48 | JH6b germline a.a. |
| 49 | JK4 germline a.a. | 50 | JK1 germline a.a. |
| 51 | Synthetic Gly-Ser linker a.a. | | |

The invention claimed is:
1. A monoclonal antibody, or an antigen binding portion thereof comprising:
   (a) a heavy chain variable region comprising amino acids having a sequence selected from the group consisting of SEQ ID NOs: 1, 2, 3 and 4; and
   (b) a light chain variable region comprising amino acids having a sequence selected from the group consisting of SEQ ID NOs: 5, 6, 7 and 8;
   wherein the antibody specifically binds to SDF-1.
2. The monoclonal antibody of claim 1, which comprises:
   (a) a heavy chain variable region comprising the amino acid sequence of SEQ ID NO: 1; and
   (b) a light chain variable region comprising the amino acid sequence of SEQ ID NO:5.
3. The monoclonal antibody of claim 1, which comprises:
   (a) a heavy chain variable region comprising the amino acid sequence of SEQ ID NO:2; and
   (b) a light chain variable region comprising the amino acid sequence of SEQ ID NO:6.
4. The monoclonal antibody of claim 1, which comprises:
   (a) a heavy chain variable region comprising the amino acid sequence of SEQ ID NO:3; and
   (b) a light chain variable region comprising the amino acid sequence of SEQ ID NO:7.
5. The monoclonal antibody of claim 1, which comprises:
   (a) a heavy chain variable region comprising the amino acid sequence of SEQ ID NO:4; and
   (b) a light chain variable region comprising the amino acid sequence of SEQ ID NO:8.
6. A monoclonal antibody, or antigen binding portion thereof, which cross-competes for binding to SDF-1 with a reference antibody, and wherein the monoclonal antibody:
   (a) binds to human SDF-1 with a KD of $1\times10^{-7}$ M or less; and
   (b) binds to human SDF-1 as detectable by an immunoprecipitation assay, and wherein the reference antibody comprises:
   (i) a heavy chain variable region comprising amino acids having the sequence set forth in SEQ ID NO: 1 and a light chain variable region comprising amino acids having the sequence set forth in SEQ ID NO: 5;
   (ii) a heavy chain variable region comprising amino acids having the sequence set forth in SEQ ID NO: 2 and a light chain variable region comprising amino acids having the sequence set forth in SEQ ID NO: 6;
   (iii) a heavy chain variable region comprising amino acids having the sequence set forth in SEQ ID NO: 3 and a light chain variable region comprising amino acids having the sequence set forth in SEQ ID NO: 7; or
   (iv) a heavy chain variable region comprising amino acids having the sequence set forth in SEQ ID NO: 4 and a light chain variable region comprising amino acids having the sequence set forth in SEQ ID NO: 8.
7. The monoclonal antibody, or antigen-binding portion thereof, of claim 6, which is a human antibody.
8. The monoclonal antibody, or antigen-binding portion thereof, of claim 6, which is a chimeric or humanized antibody.
9. The monoclonal antibody, or antigen-binding portion thereof, of claim 7, which is an antibody of an IgG1, IgG2 or IgG4 isotype or an antigen-binding portion thereof.
10. The monoclonal antibody, or antigen-binding portion thereof, of claim 7, which is an antibody fragment or a single chain antibody.
11. The monoclonal antibody, or antigen-binding portion thereof, of claim 7, wherein said antibody binds to human SDF-1 with a $K_D$ of $1\times10^{-8}$ M or less.
12. The monoclonal antibody, or antigen-binding portion thereof, of claim 7, wherein said antibody binds to human SDF-1 with a $K_D$ of $1\times10^{-9}$ M or less.
13. The monoclonal antibody, or antigen-binding portion thereof, of claim 7, wherein said antibody has a melting temperature of 57° C. or higher.
14. The monoclonal antibody, or antigen-binding portion thereof, of claim 7, wherein said antibody has a melting temperature of 68° C. or higher.
15. The monoclonal antibody, or antigen-binding portion thereof, of claim 7, wherein said antibody blocks the binding of SDF-1 to CEM cells.
16. The monoclonal antibody, or antigen-binding portion thereof, of claim 7, wherein said antibody blocks SDF-1 induced calcium flux in CEM cells.
17. The monoclonal antibody, or antigen-binding portion thereof, of claim 7, wherein said antibody blocks SDF-1 induced migration of CEM cells.
18. The monoclonal antibody, or antigen-binding portion thereof, of claim 7, wherein said antibody blocks capillary tube formation in HuVEC cells.
19. The monoclonal antibody, or antigen-binding portion thereof, of claim 7, wherein human SDF-1 comprises a polypeptide having an amino acid sequence as set forth in SEQ ID NO:44.
20. The monoclonal antibody of claim 6, which is selected from the group consisting of:
   (i) an antibody comprising:
   (a) a heavy chain variable region CDR1 comprising SEQ ID NO:9;
   (b) a heavy chain variable region CDR2 comprising SEQ ID NO:13;
   (c) a heavy chain variable region CDR3 comprising SEQ ID NO:17;
   (d) a light chain variable region CDR1 comprising SEQ ID NO:21;
   (e) a light chain variable region CDR2 comprising SEQ ID NO:25; and
   (f) a light chain variable region CDR3 comprising SEQ ID NO:29,
   (ii) an antibody comprising:
   (a) a heavy chain variable region CDR1 comprising SEQ ID NO:10;
   (b) a heavy chain variable region CDR2 comprising SEQ ID NO:14;
   (c) a heavy chain variable region CDR3 comprising SEQ ID NO:18;
   (d) a light chain variable region CDR1 comprising SEQ ID NO:22;
   (e) a light chain variable region CDR2 comprising SEQ ID NO:26; and
   (f) a light chain variable region CDR3 comprising SEQ ID NO:30,
   (iii) an antibody comprising:
   (a) a heavy chain variable region CDR1 comprising SEQ ID NO:11;
   (b) a heavy chain variable region CDR2 comprising SEQ ID NO:15;
   (c) a heavy chain variable region CDR3 comprising SEQ ID NO:19;
   (d) a light chain variable region CDR1 comprising SEQ ID NO:23;
   (e) a light chain variable region CDR2 comprising SEQ ID NO:27; and

(f) a light chain variable region CDR3 comprising SEQ ID NO:31, and
(iv) an antibody comprising:
(a) a heavy chain variable region CDR1 comprising SEQ ID NO:12;
(b) a heavy chain variable region CDR2 comprising SEQ ID NO:16;
(c) a heavy chain variable region CDR3 comprising SEQ ID NO:20;
(d) a light chain variable region CDR1 comprising SEQ ID NO:24;
(e) a light chain variable region CDR2 comprising SEQ ID NO:28; and
(f) a light chain variable region CDR3 comprising SEQ ID NO:32.

21. A composition comprising the antibody, or antigen-binding portion thereof, of claim 6, and a pharmaceutically acceptable carrier.

22. An immunoconjugate comprising the antibody, or antigen-binding portion thereof, of claim 6, linked to a therapeutic agent.

23. A composition comprising the immunoconjugate of claim 22 and a pharmaceutically acceptable carrier.

24. The immunoconjugate of claim 22, wherein the therapeutic agent is a cytotoxin.

25. A composition comprising the immunoconjugate of claim 24 and a pharmaceutically acceptable carrier.

26. The immunoconjugate of claim 22, wherein the therapeutic agent is a radioactive isotope.

27. A composition comprising the immunoconjugate of claim 26 and a pharmaceutically acceptable carrier.

28. The monoclonal antibody of claim 6, wherein the monoclonal antibody binds to both a monomeric and a dimeric form of SDF-1.

29. The monoclonal antibody of claim 6, wherein the monoclonal antibody binds to a receptor binding site on the SDF-1 protein.

30. The monoclonal antibody of claim 29, wherein the monoclonal antibody binds to amino acid residues 7-19 of the SDF-1 protein.

31. The monoclonal antibody of claim 6, wherein the monoclonal antibody binds to amino acid residues 37-50 of the SDF-1 protein.

32. The monoclonal antibody of claim 6, wherein the monoclonal antibody binds to the dimeric but not monomeric form of SDF-1.

33. The monoclonal antibody of claim 32, wherein the monoclonal antibody binds to a heparin binding site of SDF-1.

34. The monoclonal antibody of claim 32, wherein the monoclonal antibody binds to a dimerization interface of SDF-1.

35. The monoclonal antibody of claim 32, wherein the monoclonal antibody binds to amino acid residues 24-30 of SDF-1.

36. A monoclonal antibody, or an antigen-binding portion thereof, comprising a heavy chain variable region and a light chain variable region, wherein said heavy chain variable region comprises amino acids having the sequence set forth in SEQ ID NO: 41 or 42, and wherein the antibody or antigen-binding portion thereof specifically binds to SDF-1.

37. A monoclonal antibody, or an antigen-binding portion thereof, comprising a light chain variable region and a heavy chain variable region, wherein said light chain variable region comprises amino acids having the sequence set forth in SEQ ID NO: 43, and wherein the antibody or antigen-binding portion thereof specifically binds to SDF-1.

38. The monoclonal antibody or antigen-binding portion thereof of claim 37, wherein said heavy chain variable region comprises amino acids having the sequence set forth in SEQ ID NO: 41 or 42.

* * * * *